US007575923B2

(12) United States Patent
Dorken et al.

(10) Patent No.: US 7,575,923 B2
(45) Date of Patent: Aug. 18, 2009

(54) CD19XCD3 SPECIFIC POLYPEPTIDES AND USES THEREOF

(75) Inventors: Bernd Dorken, Berlin (DE); Gert Riethmuller, Munich (DE); Peter Kufer, Moosburg (DE); Ralf Lutterbuse, Munich (DE); Ralf Bargou, Berlin (DE); Anja Loffler, Finowfurt/Eichhorst (DE)

(73) Assignee: Micromet AG, Munich (DE)

( * ) Notice: Subject to any disclaimer, the term of this patent is extended or adjusted under 35 U.S.C. 154(b) by 14 days.

(21) Appl. No.: 11/418,058

(22) Filed: May 5, 2006

(65) Prior Publication Data

US 2006/0193852 A1 Aug. 31, 2006

Related U.S. Application Data

(62) Division of application No. 09/673,735, filed as application No. PCT/EP99/02693 on Apr. 21, 1999, now Pat. No. 7,112,324.

(30) Foreign Application Priority Data

Apr. 21, 1998 (EP) .................................. 98107269

(51) Int. Cl.

| | |
|---|---|
| ***C12N 5/10*** | (2006.01) |
| ***C07H 21/02*** | (2006.01) |
| ***C07H 21/04*** | (2006.01) |
| *C12P 21/08* | (2006.01) |
| *A61K 39/395* | (2006.01) |

(52) U.S. Cl. ...................... 435/328; 435/69.6; 435/332; 435/334; 424/135.1; 530/287.3; 536/23.53

(58) Field of Classification Search ............. 424/135.1; 530/387.3; 536/23.53; 435/69.6, 328, 332, 435/334

See application file for complete search history.

(56) References Cited

U.S. PATENT DOCUMENTS

| | | | | |
|---|---|---|---|---|
| 5,239,062 A | | 8/1993 | Blattler et al. | |
| 5,637,481 A | * | 6/1997 | Ledbetter et al. | 435/69.6 |
| 7,112,324 B1 | | 9/2006 | Dorken et al. | |
| 2007/0123479 A1 | | 5/2007 | Kufer et al. | |

FOREIGN PATENT DOCUMENTS

| | | |
|---|---|---|
| DE | 195 31 348 | 2/1997 |
| DE | 195 31 348 A | 2/1997 |
| EP | 0 505 908 | 9/1992 |
| WO | WO 91/09968 | 7/1991 |
| WO | WO 95/11922 | 5/1995 |
| WO | WO 96/36360 | 11/1996 |

OTHER PUBLICATIONS

Wang et al., Nuc. Acids Res. 27: 4609-4618, 1999.*
Kaufman et al, Blood 94: 3178-3184, 1999.*
Wigley et al., Reprod Fert Dev 6: 585-588, 1994.*
Phillips, A., J Pharm Pharmacology 53: 1169-1174, 2001.*
Anderson, et al., G19.4(αCD3) x B43(αCD19) Monoclonal Antibody Heteroconjugate Triggers CD19 Antigen-Specific Lysis of t(4;11) Acute Lymphoblastic Leukemia Cells by Activated CD3 Antigen-Positive Cytotoxic T Cells, *Blood*, vol. 80, No. 11, pp. 2826-2834 (1992).
Bohlen et al., "Treatment of EB-Virus Induced B-Cell LCL in SCID-HU Mice Using CD3XCD19 Bispecific and CD28 Antibodies.", *Proceedings of the American Association for Cancer Research*, vol. 35, Mar. 1994, p. 510, XP-002076122, abstract.
Bohlen, et al., "Cytolysis of Leukemic B-Cells by T-Cells Activated via Two Bispecific Antibodies", *Cancer Research*, vol. 53, pp. 4310-4314 (1993).
Bohlen, et al., *Blood*, 82:1803-12, 1993.
Csoka, et al., "Activation of T Cell Cytotoxicity Against Autologous Common Acute Lymphoblastic Leukemia (cALL) Blasts by CD3 X CD19 Bispecific Antibody", *Leukemia*, vol. 10, pp. 1765-1772 (1996).
Davis, et al., "Current Progress in the Gene Therapy of Cancer", *Current Opinion in Oncology*, vol. 8, pp. 499-508 (1996).
De Gast, et al., "Clinical Experience with CD3 x CD 19 Bispecific Antibodies in Patients with B Cell Malignancies", *J. Hema.*, vol. 4, pp. 433-437 (1995).
De Jonge et al., "Bispecific antibody treatment of murine B cell lymphoma.", *Cancer Immunology Immunotherapy*, vol. 45, No. 3/4, pp. 162-165, XP-002076120, Springer-Verlag, 1997.
De Jonge et al., "In Vivo Retargeting of T Cell Effector Function by Recombinant Bispecific Single Chain Fv (Anti-CD3 X Anti-Idiotype) Induces Long-Term Survival in the Murine BCL1 Lymphoma Model," *The Journal of Immunology*, vol. 161, pp. 1454-1461, 1998, (Exhibit 5).
De Jonge et al., "Production And Characterization Of Bispecific Single-Chain Antibody Fragments," *Molecular Immunology*, vol. 32, No. 17/18, pp. 1405-1412, 1995, (Exhibit 4).
Edelstein, et al., "Gene Therapy Clinical Trials Worldwide: 1989-2004—An Overview", *J. Gene Med.*, vol. 6, pp. 597-605 (2004).
Gruber, et al., "Efficient Tumor Cell Lysis Mediated by a Bispecific Single Chain Antibody Expressed in *Escherichia coli*", *J. of Immunology*, vol. 152, pp. 5368-5374 (1994).

(Continued)

*Primary Examiner*—Alana M. Harris
*Assistant Examiner*—Anne L Holleran
(74) *Attorney, Agent, or Firm*—Foley & Lardner LLP

(57) ABSTRACT

Described are novel single-chain multifunctional polypeptides comprising at least two binding sites specific for the CD19 and CD3 antigen, respectively. Further provided are polypeptides, wherein the above-described polypeptide comprises at least one further domain, preferably of pre-determined function. Furthermore, polynucleotides encoding said polypeptides as well as to vectors comprising said polynucleotides and host cells transformed therewith and their use in the production of said polypeptides are described. In addition, compositions, preferably pharmaceutical and diagnostic compositions are provided comprising any of the afore-described polypeptides, polynucleotides or vectors. Described is also the use of the afore-mentioned polypeptides, polynucleotides and vectors for the preparation of pharmaceutical compositions for immunotherapy, preferably against B-cell malignancies such as non-Hodgkin lymphoma.

4 Claims, 23 Drawing Sheets

OTHER PUBLICATIONS

Haagen, "Performance of CD3 x CD19 Bispecific Monoclonal Antibodies in B Cell Malignancy", *Leukemia and Lymphoma*, vol. 19, pp. 381-393 (1995).
Haagen, et al., "Killing of Autologous B-Lineage Malignancy Using CD3 x CD19 Bispecific Monoclonal Antibody in End Stage Leukemia and Lymphoma", *Blood*, vol. 84, No. pp. 556-563 (1994).
Haagen, et al., "The Efficacy of CD3 x CD19 Bispecific Monoclonal Antibody (BsAb) in a Clonogenic Assay: The Effect of Repeated Addition of BsAb and Interleukin-2", *Blood*, vol. 85, No. 11, pp. 3208-3212 (1995).
Haagen, et al., "Unprimed CD4+ and CD8+ T cells can be rapidly activated by a CD3 X CD19 bispecific antibody to proliferate and become cytotoxic", *Cancer Immunol. Immunother*, vol. 39, pp. 391-396 (1994).
Stein, et al., "Die neue WHO-Klassifikation der malignen Lymphome.", Deutsches Arzteblatt, vol. 96, pp. C-2302-C-2309, Dec. 1999, including English language summary, (Exhibit 2).
Hayden, et al., "Single-chain Mono- and Bispecific Antibody Derivatives with Novel Biological Properties and Antitumour Activity from a COS Cell Transient Expression System", *Therapeutic Immunology*, vol. 1, pp. 3-15 (1994).
Holliger, et al., "Diabodies: Small Bispecific Antibody Fragments", *Cancer Immunol. Immunother*, vol. 45, pp. 128-130 (1997).
Jonge et al., *Cancer Immunol Immunother* 45:162-165, 1997.
Kipriyanov, et al. "Rapid Detection of Recombinant Antibody Fragments Directed Against Cell-surface Antigens by Flow Cytometry", *J. of Immunological Methods*, vol. 196, pp. 51-62 (1996).
Kipriyanov, et al., "Bispecific CD3 x CD 19 Diabody for T Cell-Mediated Lysis of Malignant Human B Cells", *Int. J. Cancer*, vol. 77, pp. 763-772 (1998).
Kipriyanov, et al., "Bispecific diabody for lysis of human B-lineage leukemia cells", The Fourteenth International Conf. on Adv. In the Application of Monoclonal Antibodies in Clinical Oncology, p. 29 Thira Santorini, Greece (May 5-7, 1997).
Kipriyanov, et al., "Bispecific Tandem Diabody for Tumor Therapy with Improved Antigen Binding and Pharmacokinetics", *J. Mol. Biol*., vol. 293, pp. 41-56 (1999).
Kostelny, "Formation of a Bispecific Antibody by the Use of Leucine Zippers", *J. of Immunology*, vol. 148, No. 5, pp. 1547-1553 (1992).
Kufer et al., "Construction and biological activity of a recombinant bispecific single-chain antibody designed for therapy of minimal residual colorectal cancer.", *Cancer Immunology Immunotherapy*, vol. 45, No. 3/4, pp. 193-197, XP-002076121, Springer-Verlag, 1997.
Kumar et al., 3rd Edition, Clinical Medicine, pp. 369-370, Bailliere Tindall, (Exhibit 3), 1994.
Loffler, et al. "A Recombinant Bispecific Single-Chain Antibody, CD19 X CD3, Induces Rapid and High Lymphoma-directed Cytotoxicity by Unstimulated T Lymphocytes", *Blood*, vol. 95, No. 6, pp. 2098-2103 (2000).
Mack et al., "Biologic Properties of a Bispecific Single-Chain Antibody Directed Against 17-1A (EpCAM) and CD3.", *Proceedings of the National Academy of Science*, vol. 92, pp. 7021-7025, 1995, (Exhibit 6).
Mack, M., et al., "A small bispecific antibody construct expressed as a functional single-chain molecule with high tumor cell cytotoxicity", *Pro. Natl. Acad. Sci*., vol. 92, pp. 7021-7025 (1995).
Olsen et al., *Hybridoma and Hybridomics*, 22:65, 2003.
Pezzutto, et al., "CD19 Monoclonal Antibody HD37 Inhibits Anti-Immunoglobulin-induced B Cell Activation and Proliferation", *J. of Immunology*, vol. 138, No. 9, pp. 2793-2799 (1997).
Reusch, et al., "Effect of Tetravalent Bispecific CD19 X CD3 Recombinant Antibody Construct and CD28 Costimulation of Lysis of Malignant B Cells from Patients with Chronic Lymphocytic Leukemia by Autologous T Cells", *Int. J. Cancer*, vol. 112, pp. 509-518 (2004).
Rudikoff, et al., *PNAS*, 79:1979, 1982.
Schroder et al., "A Recombinant Bispecific Single Chain Antibody Cd19xcd3 Induced Rapid B Cell Lymphoma-Directed Cytotoxicity Of Unstimulated Human T Cells," 40th Annual Meeting Of The American Society Of Hematology Miami Beach, Florida, Dec. 4-8, 1998, XP-002115457, abstract.
Sompuram, et al., *The Journal of Immunology*, 156: 1071-81, 1996.
Traunecker, et al. "Janusin: New Molecular Design for Bispecific Reagents", *Int. J. Cancer*, Suppl. 7, pp. 51-52 (1992).
Weiner, et al., "Bispecific Monoclonal Antibody Therapy of B-Cell Malignancy", *Leukemia and Lymphoma*, vol. 16, pp. 199-207 (1995).
Weiner, et al., "The Role of T Cell Activation in Anti-CD3 X Antitumor Bispecific Antibody Therapy", *J. of Immunology*, vol. 152, pp. 2385-2392 (1994).
"National Cancer Institute Sponsored Study of Classifications of Non-Hodgkin's Lymphomas, Summary and Description of a Working Formulation for Clinical Usage.", Cancer, vol. 49, pp. 2112-2135, 1982, (Exhibit 1).
Lindhofer et al., International Application No. WO 97/08205, cover page with English Abstract, Mar. 6, 1997.

* cited by examiner

Coomassie Blue–stained SDS/Polyacrylamide Gel of Purified bscCD19xCD3

Inhibition of the cytotoxicity of bscCD19xCD3 by the parental anti-CD19 antibody HD37

Figure 8:

```
                                                      -10     -5   -1
                                                   5' G AAT TCC ACC

        9           18          27          36          45          54
ATG GGA TGG AGC TGT ATC ATC CTC TTC TTG GTA GCA ACA GCT ACA GGT GTC CAC
--- --- --- --- --- --- --- --- --- --- --- --- --- --- --- --- --- ---
 M   G   W   S   C   I   I   L   F   L   V   A   T   A   T   G   V   H

        63          72          81          90          99          108
TCC GAC TAC AAA GAT GAT GAC GAT AAG GAT ATC CAG CTG ACC CAG TCT CCA GCT
--- --- --- --- --- --- --- --- --- --- --- --- --- --- --- --- --- ---
 S   D   Y   K   D   D   D   D   K   D   I   Q   L   T   Q   S   P   A

        117         126         135         144         153         162
TCT TTG GCT GTG TCT CTA GGG CAG AGG GCC ACC ATC TCC TGC AAG GCC AGC CAA
--- --- --- --- --- --- --- --- --- --- --- --- --- --- --- --- --- ---
 S   L   A   V   S   L   G   Q   R   A   T   I   S   C   K   A   S   Q

        171         180         189         198         207         216
AGT GTT GAT TAT GAT GGT GAT AGT TAT TTG AAC TGG TAC CAA CAG ATT CCA GGA
--- --- --- --- --- --- --- --- --- --- --- --- --- --- --- --- --- ---
 S   V   D   Y   D   G   D   S   Y   L   N   W   Y   Q   Q   I   P   G

        225         234         243         252         261         270
CAG CCA CCC AAA CTC CTC ATC TAT GAT GCA TCC AAT CTA GTT TCT GGG ATC CCA
--- --- --- --- --- --- --- --- --- --- --- --- --- --- --- --- --- ---
 Q   P   P   K   L   L   I   Y   D   A   S   N   L   V   S   G   I   P

        279         288         297         306         315         324
CCC AGG TTT AGT GGC AGT GGG TCT GGG ACA GAC TTC ACC CTC AAC ATC CAT CCT
--- --- --- --- --- --- --- --- --- --- --- --- --- --- --- --- --- ---
 P   R   F   S   G   S   G   S   G   T   D   F   T   L   N   I   H   P

        333         342         351         360         369         378
GTG GAG AAG GTG GAT GCT GCA ACC TAT CAC TGT CAG CAA AGT ACT GAG GAT CCG
--- --- --- --- --- --- --- --- --- --- --- --- --- --- --- --- --- ---
 V   E   K   V   D   A   A   T   Y   H   C   Q   Q   S   T   E   D   P

        387         396         405         414         423         432
TGG ACG TTC GGT GGA GGG ACC AAG CTC GAG ATC AAA GGT GGT GGT GGT TCT GGC
--- --- --- --- --- --- --- --- --- --- --- --- --- --- --- --- --- ---
 W   T   F   G   G   G   T   K   L   E   I   K   G   G   G   G   S   G

        441         450         459         468         477         486
GGC GGC GGC TCC GGT GGT GGT GGT TCT CAG GTG CAG CTG CAG CAG TCT GGG GCT
--- --- --- --- --- --- --- --- --- --- --- --- --- --- --- --- --- ---
 G   G   G   S   G   G   G   G   S   Q   V   Q   L   Q   Q   S   G   A

        495         504         513         522         531         540
GAG CTG GTG AGG CCT GGG TCC TCA GTG AAG ATT TCC TGC AAG GCT TCT GGC TAT
--- --- --- --- --- --- --- --- --- --- --- --- --- --- --- --- --- ---
 E   L   V   R   P   G   S   S   V   K   I   S   C   K   A   S   G   Y

        549         558         567         576         585         594
GCA TTC AGT AGC TAC TGG ATG AAC TGG GTG AAG CAG AGG CCT GGA CAG GGT CTT
--- --- --- --- --- --- --- --- --- --- --- --- --- --- --- --- --- ---
 A   F   S   S   Y   W   M   N   W   V   K   Q   R   P   G   Q   G   L

        603         612         621         630         639         648
GAG TGG ATT GGA CAG ATT TGG CCT GGA GAT GGT GAT ACT AAC TAC AAT GGA AAG
--- --- --- --- --- --- --- --- --- --- --- --- --- --- --- --- --- ---
 E   W   I   G   Q   I   W   P   G   D   G   D   T   N   Y   N   G   K

        657         666         675         684         693         702
TTC AAG GGT AAA GCC ACT CTG ACT GCA GAC GAA TCC TCC AGC ACA GCC TAC ATG
--- --- --- --- --- --- --- --- --- --- --- --- --- --- --- --- --- ---
 F   K   G   K   A   T   L   T   A   D   E   S   S   S   T   A   Y   M

        711         720         729         738         747         756
CAA CTC AGC AGC CTA GCA TCT GAG GAC TCT GCG GTC TAT TTC TGT GCA AGA CGG
--- --- --- --- --- --- --- --- --- --- --- --- --- --- --- --- --- ---
 Q   L   S   S   L   A   S   E   D   S   A   V   Y   F   C   A   R   R
```

Figure 8 (continued)

```
        765         774         783         792         801         810
GAG ACT ACG ACG GTA GGC CGT TAT TAC TAT GCT ATG GAC TAC TGG GGC CAA GGG
--- --- --- --- --- --- --- --- --- --- --- --- --- --- --- --- --- ---
 E   T   T   T   V   G   R   Y   Y   Y   A   M   D   Y   W   G   Q   G

        819         828         837         846         855         864
ACC ACG GTC ACC GTC TCC TCC GGA GGT GGT GGA TCC GAT ATC AAA CTG CAG CAG
--- --- --- --- --- --- --- --- --- --- --- --- --- --- --- --- --- ---
 T   T   V   T   V   S   S   G   G   G   G   S   D   I   K   L   Q   Q

        873         882         891         900         909         918
TCA GGG GCT GAA CTG GCA AGA CCT GGG GCC TCA GTG AAG ATG TCC TGC AAG ACT
--- --- --- --- --- --- --- --- --- --- --- --- --- --- --- --- --- ---
 S   G   A   E   L   A   R   P   G   A   S   V   K   M   S   C   K   T

        927         936         945         954         963         972
TCT GGC TAC ACC TTT ACT AGG TAC ACG ATG CAC TGG GTA AAA CAG AGG CCT GGA
--- --- --- --- --- --- --- --- --- --- --- --- --- --- --- --- --- ---
 S   G   Y   T   F   T   R   Y   T   M   H   W   V   K   Q   R   P   G

        981         990         999        1008        1017        1026
CAG GGT CTG GAA TGG ATT GGA TAC ATT AAT CCT AGC CGT GGT TAT ACT AAT TAC
--- --- --- --- --- --- --- --- --- --- --- --- --- --- --- --- --- ---
 Q   G   L   E   W   I   G   Y   I   N   P   S   R   G   Y   T   N   Y

       1035        1044        1053        1062        1071        1080
AAT CAG AAG TTC AAG GAC AAG GCC ACA TTG ACT ACA GAC AAA TCC TCC AGC ACA
--- --- --- --- --- --- --- --- --- --- --- --- --- --- --- --- --- ---
 N   Q   K   F   K   D   K   A   T   L   T   T   D   K   S   S   S   T

       1089        1098        1107        1116        1125        1134
GCC TAC ATG CAA CTG AGC AGC CTG ACA TCT GAG GAC TCT GCA GTC TAT TAC TGT
--- --- --- --- --- --- --- --- --- --- --- --- --- --- --- --- --- ---
 A   Y   M   Q   L   S   S   L   T   S   E   D   S   A   V   Y   Y   C

       1143        1152        1161        1170        1179        1188
GCA AGA TAT TAT GAT GAT CAT TAC TGC CTT GAC TAC TGG GGC CAA GGC ACC ACT
--- --- --- --- --- --- --- --- --- --- --- --- --- --- --- --- --- ---
 A   R   Y   Y   D   D   H   Y   C   L   D   Y   W   G   Q   G   T   T

       1197        1206        1215        1224        1233        1242
CTC ACA GTC TCC TCA GTC GAA GGT GGA AGT GGA GGT TCT GGT GGA AGT GGA GGT
--- --- --- --- --- --- --- --- --- --- --- --- --- --- --- --- --- ---
 L   T   V   S   S   V   E   G   G   S   G   G   S   G   G   S   G   G

       1251        1260        1269        1278        1287        1296
TCA GGT GGA GTC GAC GAC ATT CAG CTG ACC CAG TCT CCA GCA ATC ATG TCT GCA
--- --- --- --- --- --- --- --- --- --- --- --- --- --- --- --- --- ---
 S   G   G   V   D   D   I   Q   L   T   Q   S   P   A   I   M   S   A

       1305        1314        1323        1332        1341        1350
TCT CCA GGG GAG AAG GTC ACC ATG ACC TGC AGA GCC AGT TCA AGT GTA AGT TAC
--- --- --- --- --- --- --- --- --- --- --- --- --- --- --- --- --- ---
 S   P   G   E   K   V   T   M   T   C   R   A   S   S   S   V   S   Y

       1359        1368        1377        1386        1395        1404
ATG AAC TGG TAC CAG CAG AAG TCA GGC ACC TCC CCC AAA AGA TGG ATT TAT GAC
--- --- --- --- --- --- --- --- --- --- --- --- --- --- --- --- --- ---
 M   N   W   Y   Q   Q   K   S   G   T   S   P   K   R   W   I   Y   D

       1413        1422        1431        1440        1449        1458
ACA TCC AAA GTG GCT TCT GGA GTC CCT TAT CGC TTC AGT GGC AGT GGG TCT GGG
--- --- --- --- --- --- --- --- --- --- --- --- --- --- --- --- --- ---
 T   S   K   V   A   S   G   V   P   Y   R   F   S   G   S   G   S   G

       1467        1476        1485        1494        1503        1512
ACC TCA TAC TCT CTC ACA ATC AGC AGC ATG GAG GCT GAA GAT GCT GCC ACT TAT
--- --- --- --- --- --- --- --- --- --- --- --- --- --- --- --- --- ---
 T   S   Y   S   L   T   I   S   S   M   E   A   E   D   A   A   T   Y

       1521        1530        1539        1548        1557        1566
TAC TGC CAA CAG TGG AGT AGT AAC CCG CTC ACG TTC GGT GCT GGG ACC AAG CTG
--- --- --- --- --- --- --- --- --- --- --- --- --- --- --- --- --- ---
 Y   C   Q   Q   W   S   S   N   P   L   T   F   G   A   G   T   K   L

       1575        1584        1593
GAG CTG AAA CAT CAT CAC CAT CAT CAT TAG TCG AC 3
--- --- --- --- --- --- --- --- --- ---
 E   L   K   H   H   H   H   H   H   *
```

Figure 10 Purification of bscCD19xCD3

Figure 11 SDS-PAGE Analysis of bscCD19xCD3

Figure 16
A
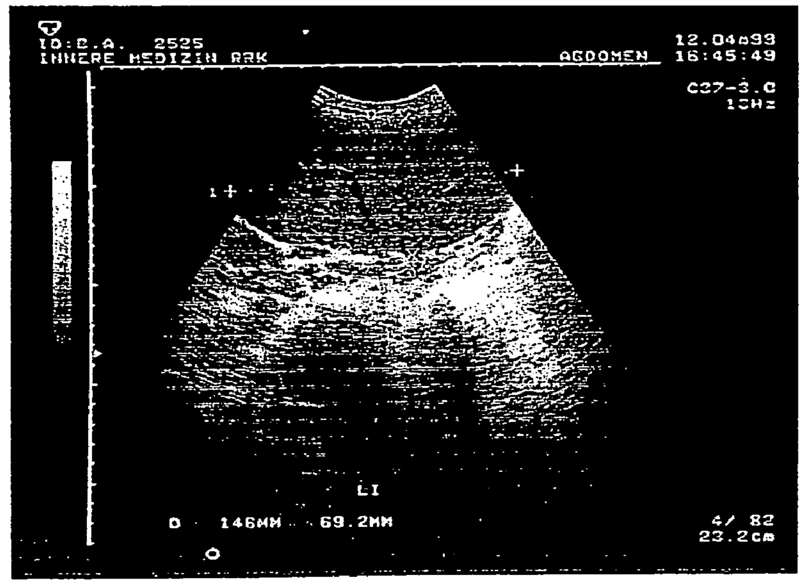
B
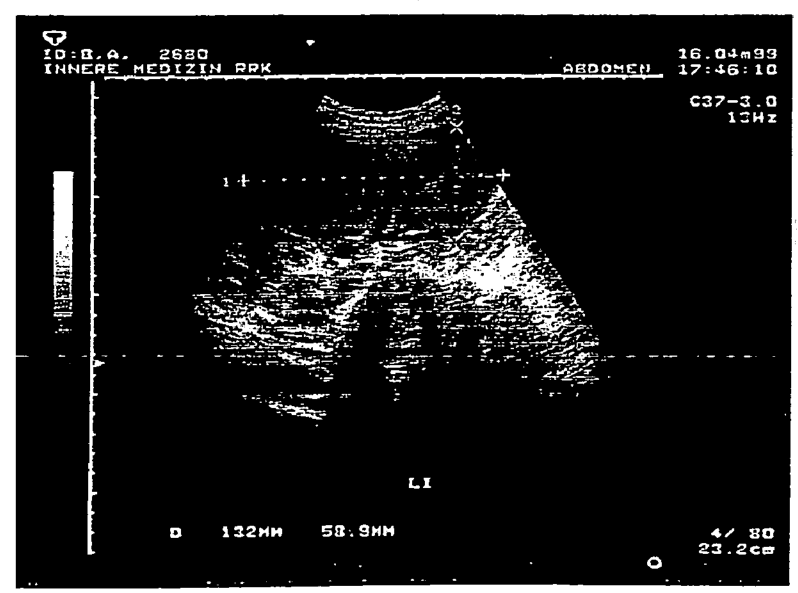

CD19XCD3 SPECIFIC POLYPEPTIDES AND USES THEREOF

CROSS-REFERENCE TO RELATED PATENT APPLICATIONS

This application claims is a Divisional Application of U.S. application Ser. No. 09/673,735 filed Dec. 27, 2000, which is a National Stage of PCT/EP99/02693 filed Apr. 21, 1999, which claims priority to E.P.O. Application No. 98107269.7 filed Apr. 21, 1998, all of which are hereby incorporated herein by reference.

BACKGROUND OF THE INVENTION

The present invention relates to novel single-chain multi-functional polypeptides comprising at least two binding sites specific for the CD19 and CD3 antigens, respectively. The present invention further relates to a polypeptide, wherein the above-described polypeptide comprises at least one further domain, preferably of pre-determined function. Furthermore, the present invention relates to polynucleotides encoding said polypeptides as well as to vectors comprising said polynucleotides and to host cells transformed therewith and their use in the production of said polypeptides. In addition, the present invention relates to compositions, preferably pharmaceutical and diagnostic compositions, comprising any of the afore-described polypeptides, polynucleotides or vectors. A further object of the present invention is the use of the afore-mentioned polypeptides, polynucleotides and vectors for the preparation of pharmaceutical compositions for immunotherapy, preferably against B-cell malignancies such as non-Hodgkin lymphoma.

Several documents are cited throughout the text of this specification. Each of the documents cited herein (including any manufacturer's specifications, instructions, etc.) are hereby incorporated by reference; however, there is no admission that any document cited is indeed prior art of the present invention.

Despite the medical importance, research in B-cell mediated diseases such as non-Hodgkin lymphoma has produced only a small number of clinically usable data and conventional approaches to cure such diseases remain tedious and unpleasant and/or have a high risk of relapse. For example, although high dose chemotherapy as a primary treatment for high grade non-Hodgkin lymphoma may improve overall survival, about 50% of the patients still die of this disease (2-4). Moreover, low-grade non-Hodgkin lymphoma-like chronic lymphatic leukemia and mantle cell lymphoma are still incurable. This has stimulated the search for alternative strategies like immunotherapy. Antibodies directed against cell surface molecules defined by CD antigens represent a unique opportunity for the development of therapeutic reagents.

The expression of certain CD antigens is highly restricted to specific lineage lymphohematopoietic cells and over the past several years, antibodies directed against lymphoid-specific antigens have been used to develop treatments that were effective either in vitro or in animal models (5-13). In this respect CD19 has proved to be a very useful target. CD19 is expressed in the whole B lineage from the pro B cell to the mature B cell, it is not shed, is uniformly expressed on all lymphoma cells, and is absent from stem cells (8, 14). An interesting modality is the application of a bispecific antibody with one specificity for CD19 and the other for the CD3 antigen on T cells. However, bispecific antibodies thus far available suffer from low T-cell cytotoxicity and the need of costimulatory agents in order to display satisfactory biological activity.

Thus, the technical problem underlying the present invention was to provide means and methods useful for the treatment of B-cell mediated diseases such as various forms of non-Hodgkin lymphoma. The solution to said technical problem is achieved by providing the embodiments characterized in the claims.

Accordingly, the present invention relates to a single-chain multi-functional polypeptide comprising (a) a first domain comprising a binding-site of an immunoglobulin chain or an antibody specifically recognizing the CD19 antigen; and (b) a second domain comprising a binding site of an immunoglobulin chain or an antibody specifically recognizing the CD3 antigen.

BRIEF DESCRIPTION OF THE DRAWINGS

FIG. 8: DNA- and protein-sequence (SEQ ID NOS:9-10) of the bscCD19×CD3 antibody (FLAG-tag containing variant). Numbers indicate the nucleotide (nt) positions, the corresponding amino acid sequence is depicted below the nucleotide sequence. The encoding DNA sequence for the bispecific antibody starts at position 1 and ends at position 1593. The first six nt (position −10 to −5) and the last six nt (position 1596 to 1601) contain the restriction enzyme cleavage sites for EcoRI and SalI, respectively. Nucleotides 1 to 57 specify the leader sequence; nucleotide 82 to 414 and 460 to 831 encode $V_L$CD19 and $V_H$CD19, respectively; nucleotide 847 to 1203 and 1258 to 1575 encode $V_H$CD3 and $V_L$CD3, respectively; and nucleotides 1576 to 1593 encode a His-tag.

A) Starting-point (t=0): n=3×106 PBL/well were seeded into a 24-well tissue culture plate in a volume of 1 ml RPMI 1640 medium each, supplemented with 10% FCS each. The initial percentage of $CD19^+$ B-cells as well as that of $CD4^+$- and $CD8^+$ T-cells is indicated.

B-G) Relative B- and $CD4^+$- and $CD8^+$ T-cell counts after t=5 days of incubation at 37° C./5% $CO_2$ in the absence (B-C) or presence (D-G) of bscCD19×CD3 (concentrations as indicated) with or without 60 U/ml IL-2. Negative controls contained either bispecific single chain antibody (17-1A×CD3) with irrelevant target cell specificity or no bispecific antibody at all (C).

Figure 10:
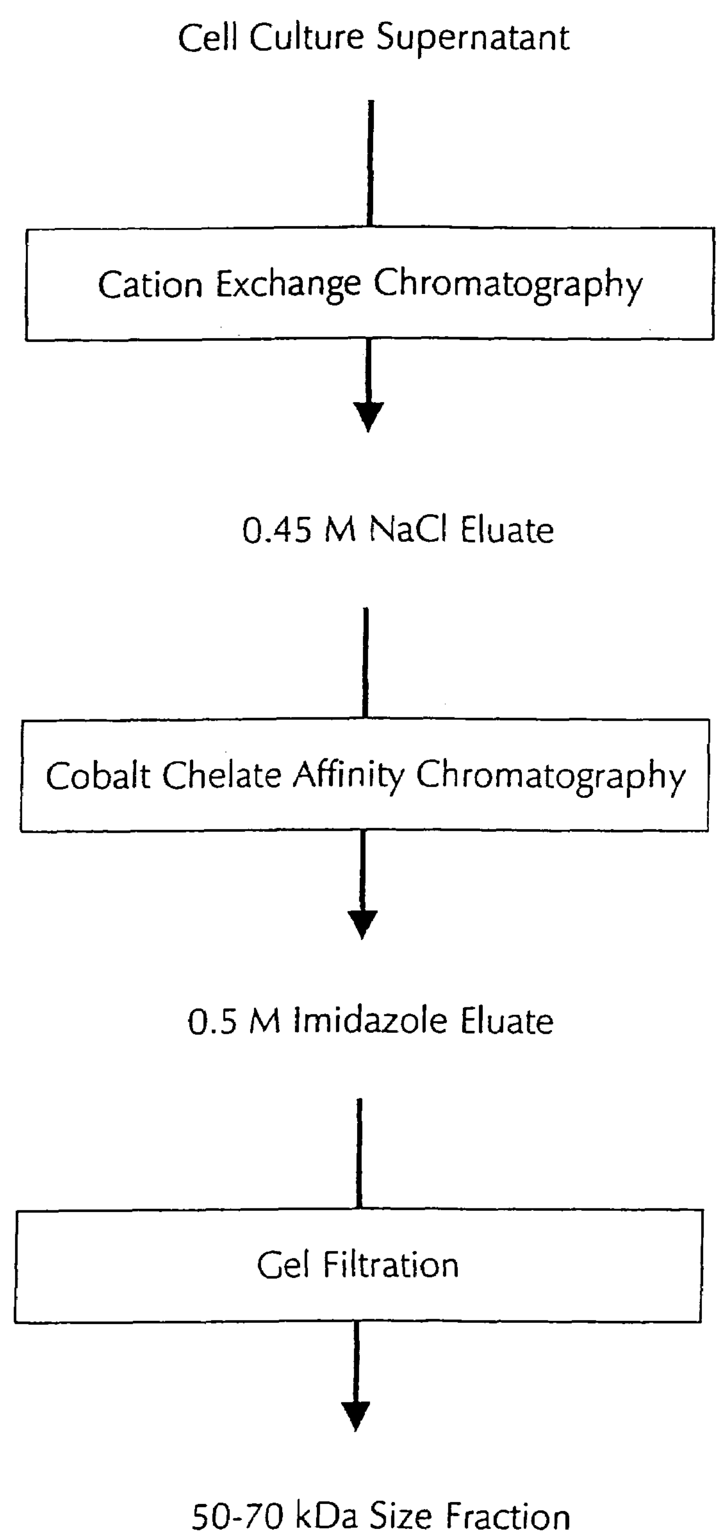

FIG. 10: Purification steps for bscCD19×CD3

Figure 11:
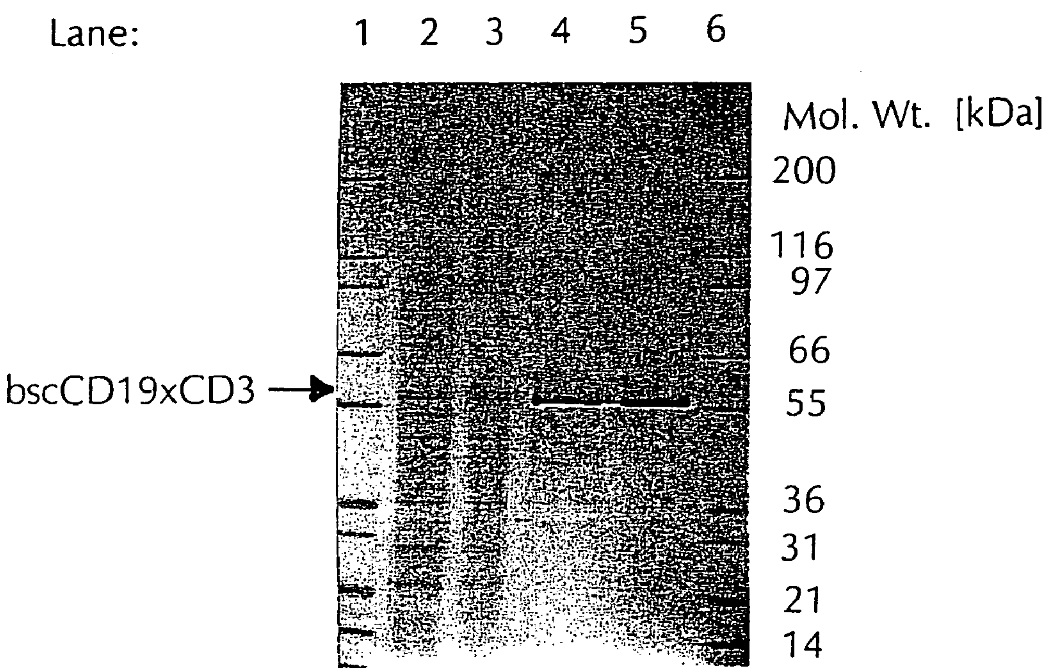

FIG. 11: SDS-PAGE analysis for the purity of bscCD19×CD3. A colloidal Coomassie-blue stained SDS 4-12% gradient polyacrylamide gel is shown. Lanes 1 and 6, molecular size markers; lane 2, cell culture supernatant; lane 3, active fraction from cation exchange chromatography; lane 4; active fraction from cobalt chelate affinity chromatography; lane 5, active fraction from gel filtration. Equal amounts of protein (2 μg) from the cell culture supernatant and the various column fractions were analyzed. The size in kDa of molecular weight standards is indicated on the right. The arrow shows the position of bscCD19×CD3.

Figure 12:
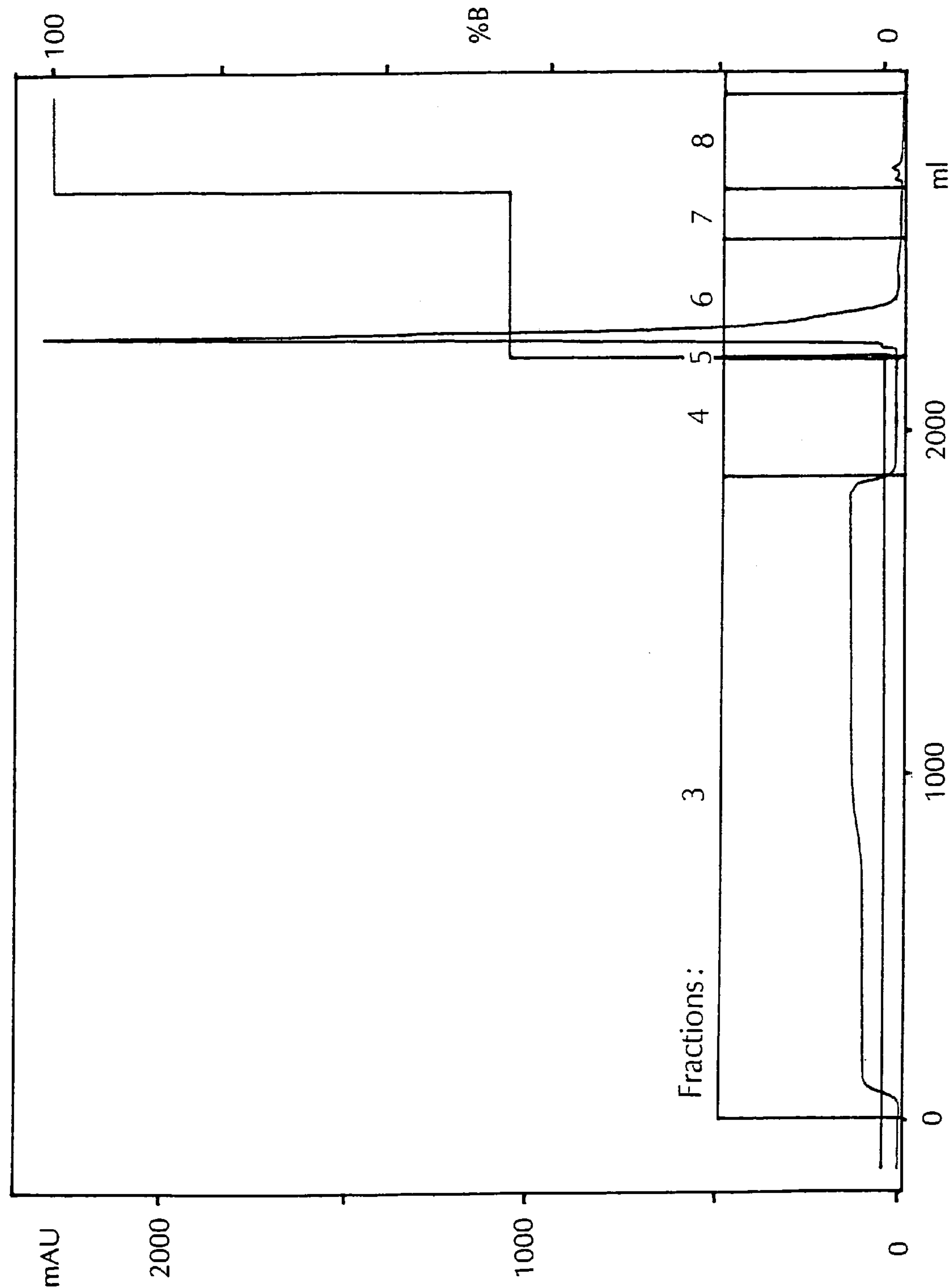

FIG. 12: Cation exchange chromatography of bscCD19×CD3. Protein concentration was measured by absorption at 280 nm (mAU, left). The elution profile of protein is shown by the solid line. The profile of the NaCl step gradient is shown by the straight solid line (% B, right) and the fractions collected are indicated by the broken lines. BscCD19×CD3 was detected in fraction F6.

Figure 13:
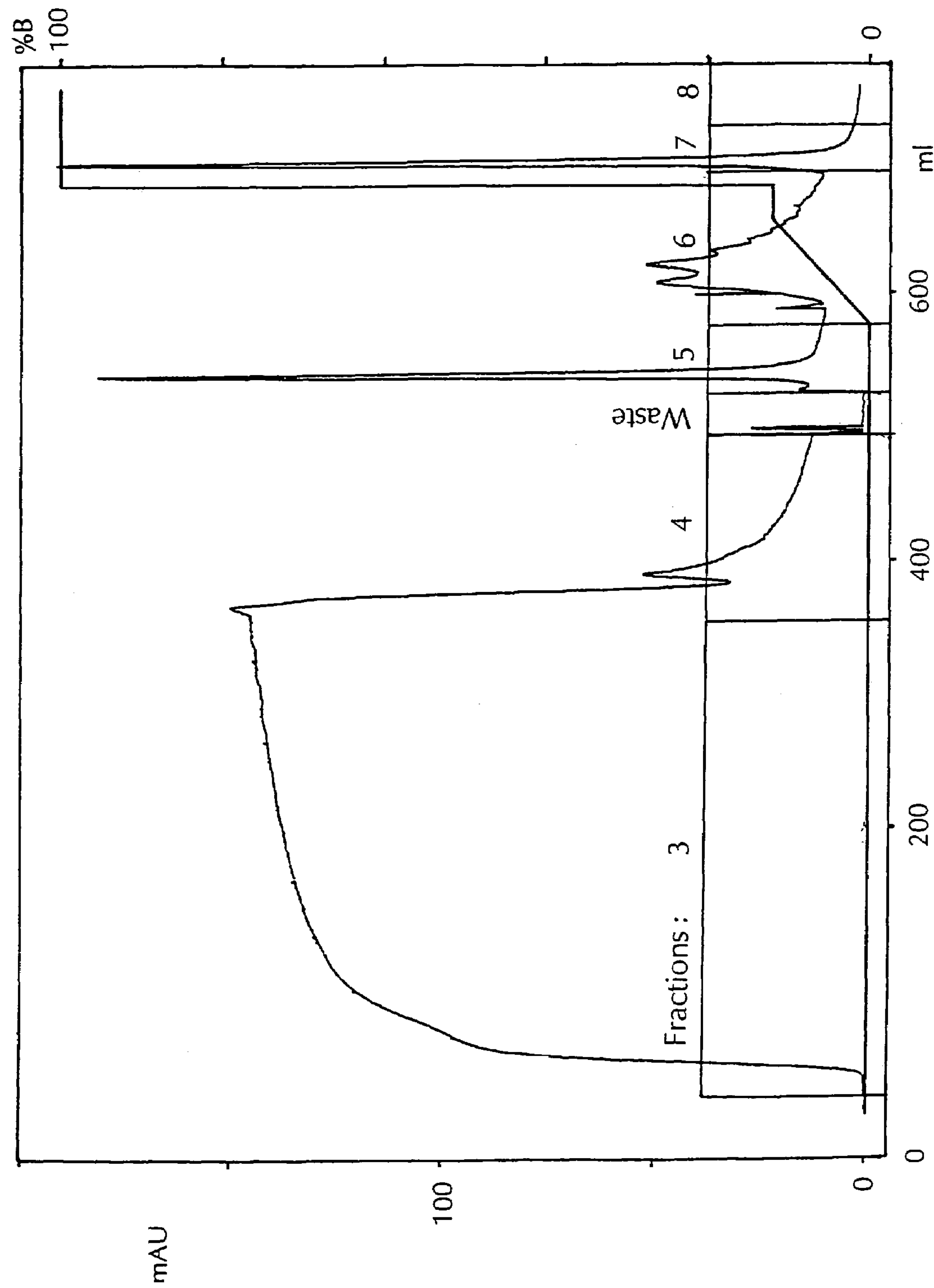

FIG. 13: Cobalt chelate affinity chromatography of bscCD19×CD3. Protein concentration was measured by absorption at 280 nm (mAU, left). The elution profile of protein is shown by the solid line. The imidazole gradient is shown by the straight solid line (% B, right) and the fractions collected are indicated by the broken lines. BscCD19×CD3 was detected in fraction F7.

Figure 14:
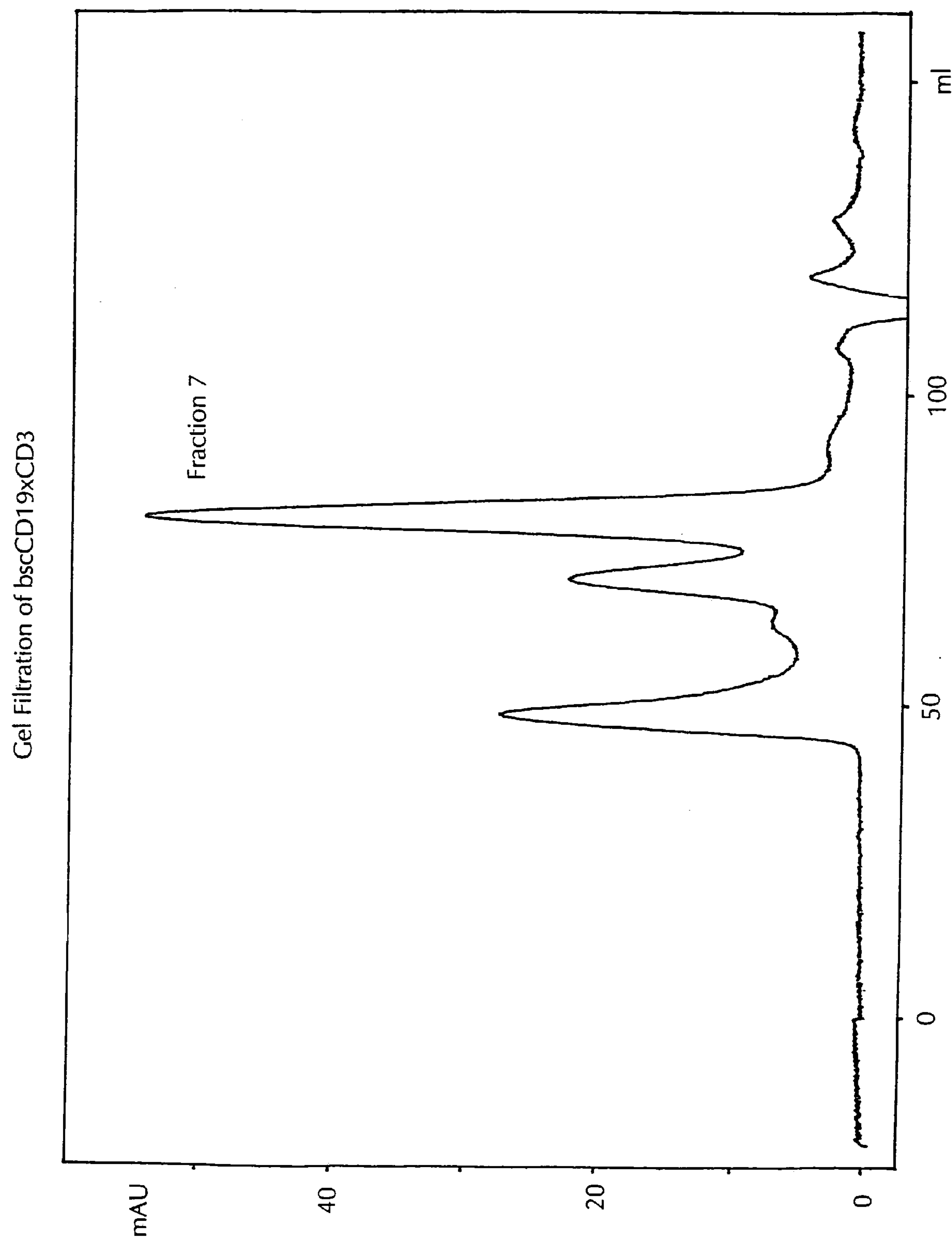

FIG. 14: Gel filtration of anti-CD19× anti-CD3. Protein concentration was measured by absorption at 280 nm (mAU, left). The elution profile of protein is shown by the solid line. Broken lines indicate the fractions collected. BscCD19×CD3 was found in fraction F7 corresponding to a molecular size of approximately 60 kDa.

Figure 15:
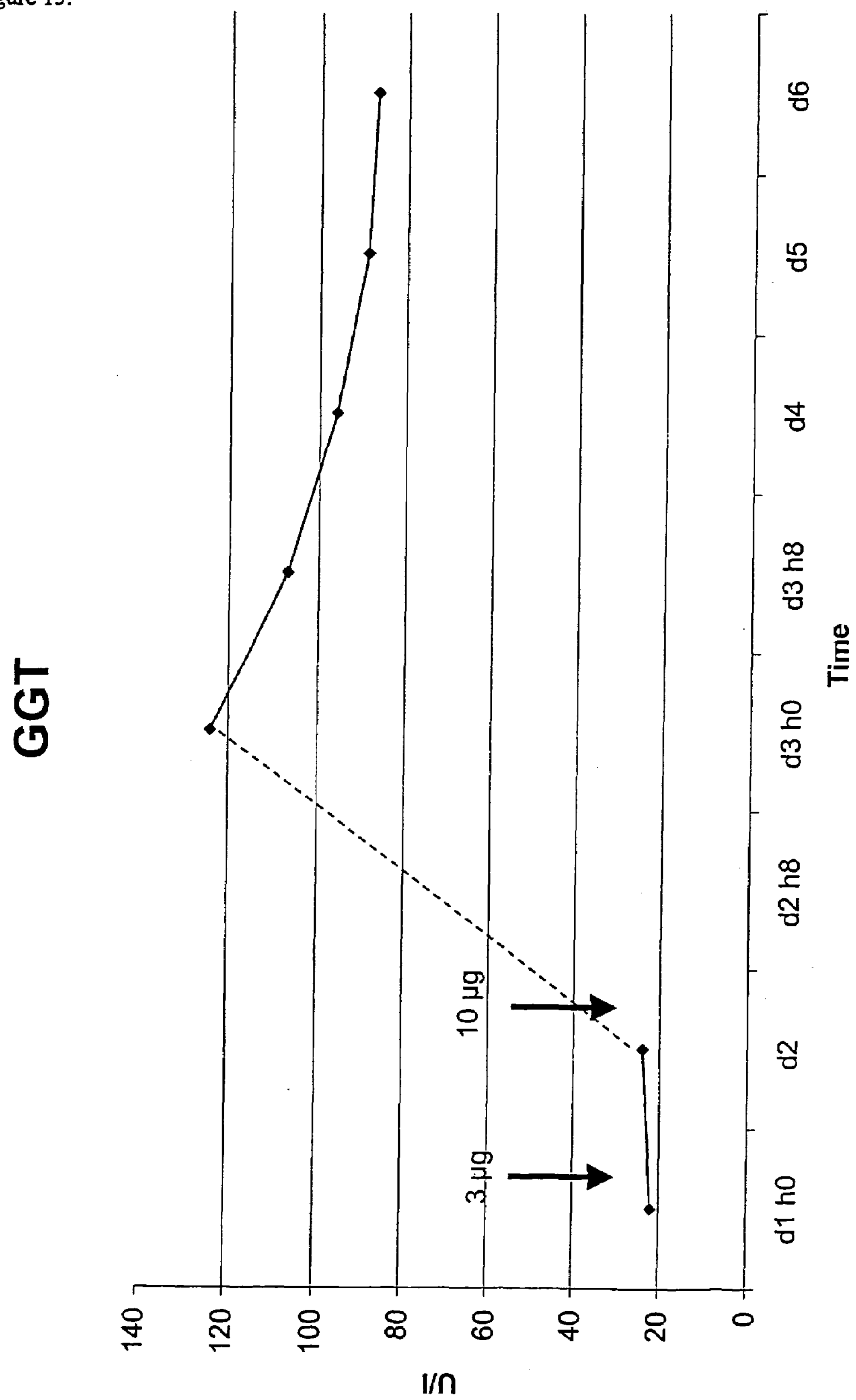

FIG. 15: Blood levels of gamma-glutamyl transferase (GGT) in response to treatments with bscCD19×CD3. GGT levels were determined by a standard clinical biochemistry method and are expressed as unit/I. The time axis shows days (d) after the onset of first drug treatment and, starting with zero, hours (h) following the individual drug additions. Arrows indicate the time points of drug administration.

FIG. 16: Ultrasound measurements of the spleen of patient A-B.

A: Determination of spleen size dated Apr. 12, 1999, prior to bscCD19×CD3 therapy. The figure shows the enlarged spleen (size 146 mm×69.2 mm) which is due to the infiltration with malignant B cells.

B: Determination of spleen size dated Apr. 16, 1999 after treatment with 3 μg on April, 14th followed by 10 μg on April 15th. The figure demonstrates shrinkage of the spleen to a size of 132 mm×58.9 mm caused by systemic treatment with bscCD19×CD3. Discrepancies of single measurements to size values depicted in Table 1 are explained by ultrasound-based organ size determination in different spatial plains. The two dimensions are marked by (+) and (×).

Figure 17:
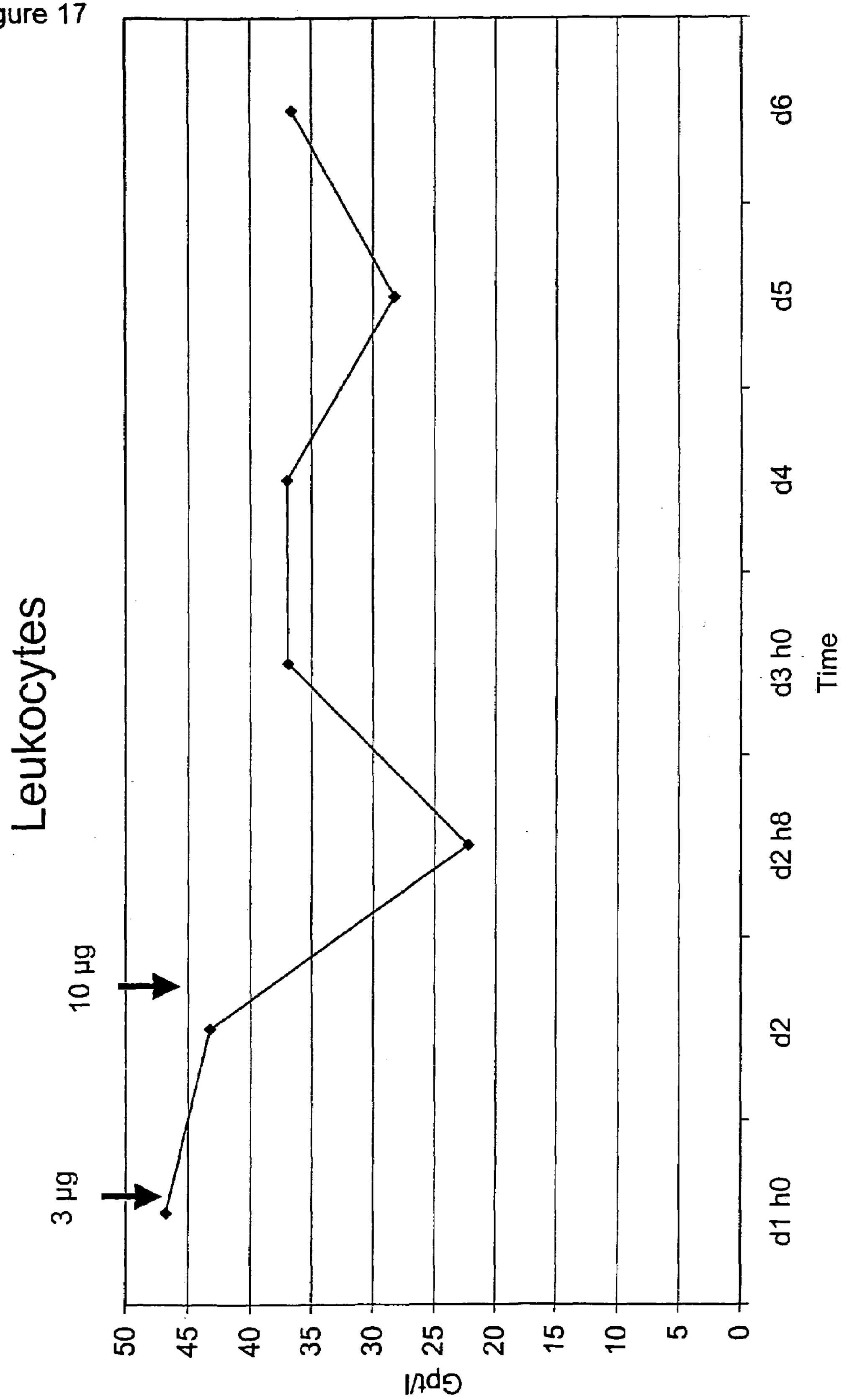

FIG. 17: Blood leukocyte counts in response to treatments with bscCD19×CD3. The number of leukocytes is given as Giga parts/liter. The time axis shows days (d) after the onset of first drug treatment and, starting with zero, hours (h) following the individual drug additions. Arrows indicate the time points of drug administration.

Figure 18:
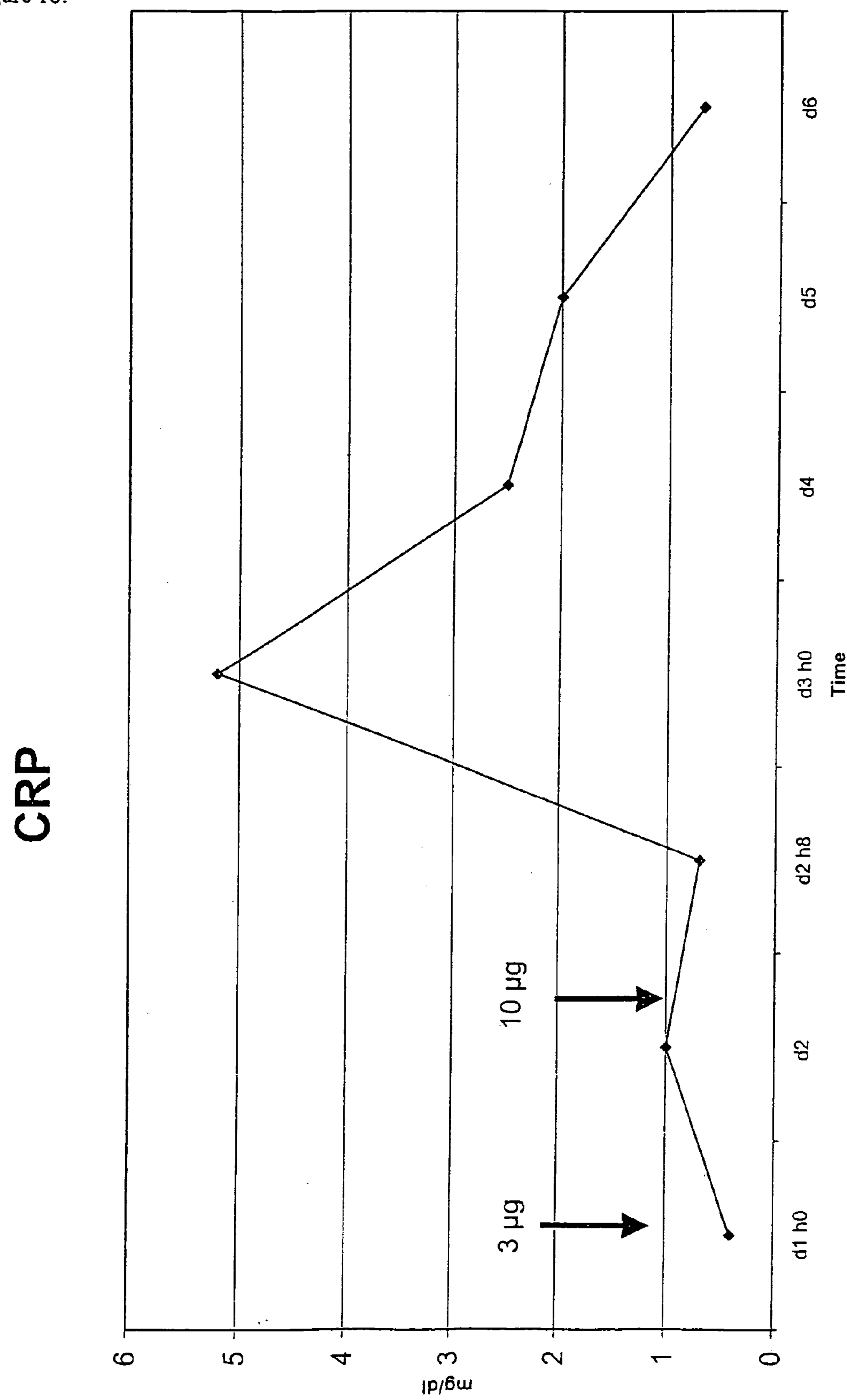

FIG. 18: Blood levels of C-reactive protein (CRP)) in response to treatments with bscCD19×CD3. CRP levels were determined by a standard clinical biochemistry method and are expressed as mg/dl. The time axis shows days (d) after the onset of first drug treatment and, starting with zero, hours (h) following the individual drug additions. Arrows indicate the time points of drug administration.

Figure 19:
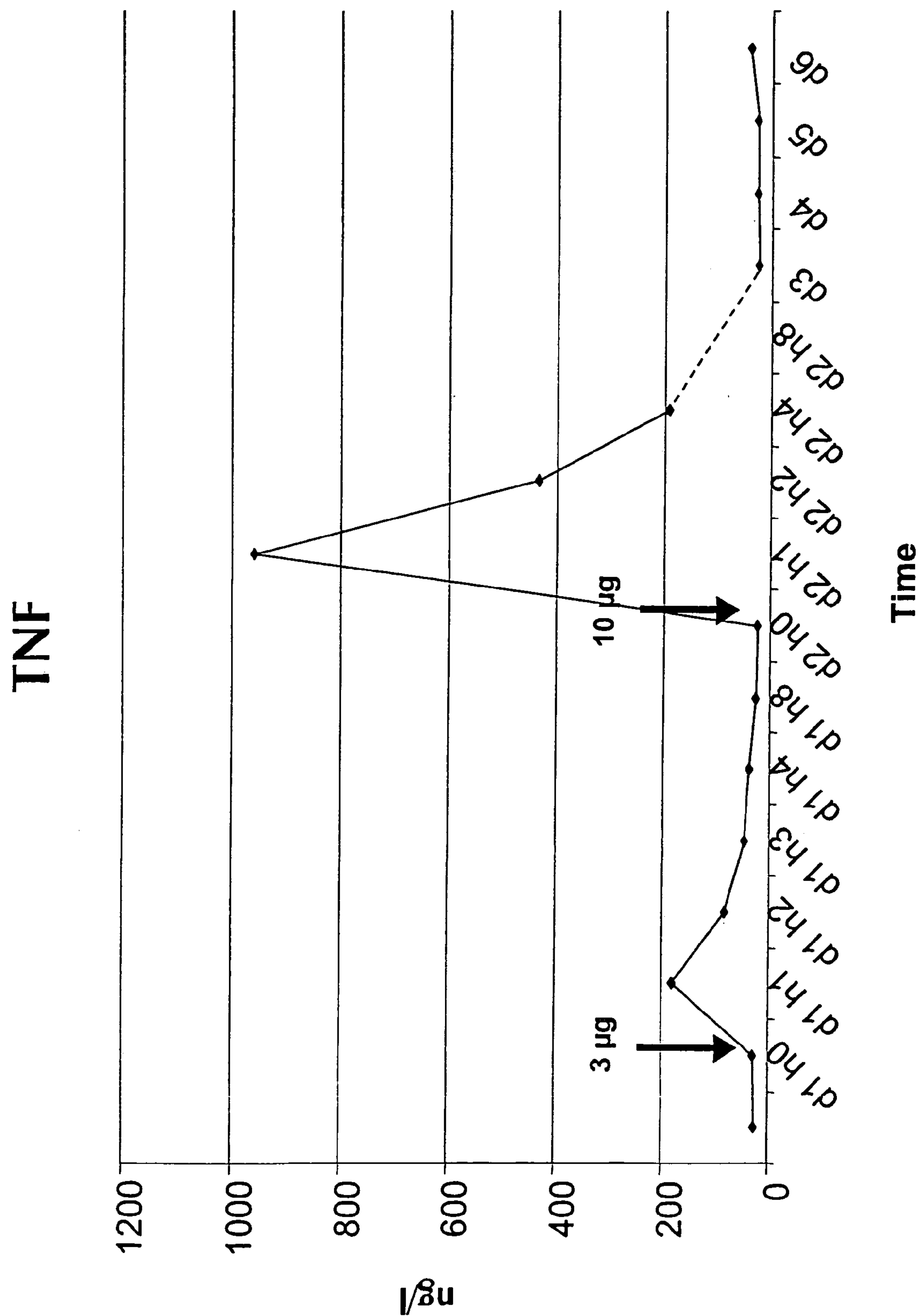

FIG. 19: Blood levels of tumor necrosis factor-alpha (TNF) in response to treatments with bscCD19×CD3. TNF levels were determined by ELISA and are expressed as ng/ml. The time axis shows days (d) after the onset of first drug treatment and, starting with zero, hours (h) following the individual drug additions. Arrows indicate the time points of drug administration.

Figure 20:
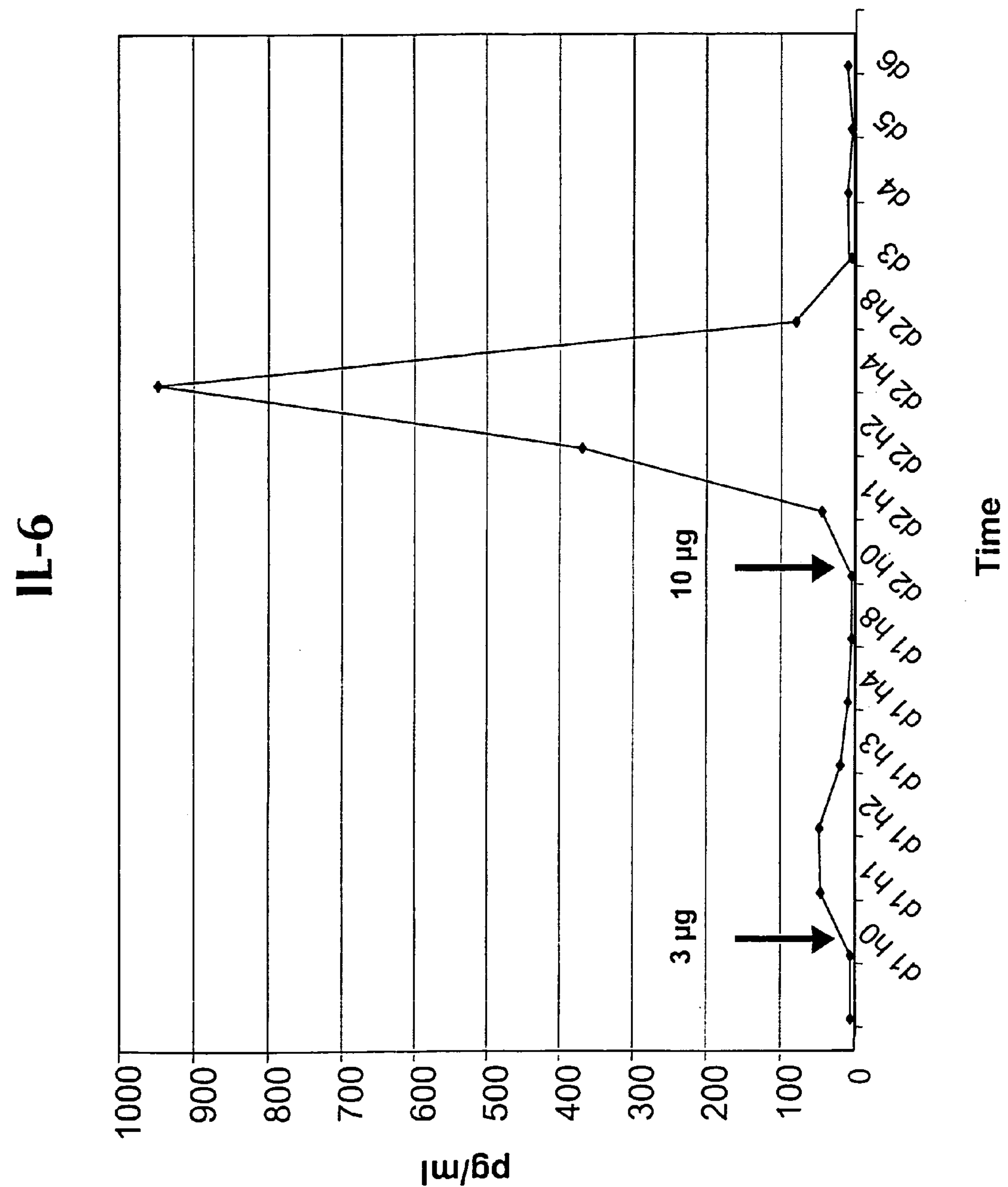

FIG. 20: Blood levels of interleukin-6 (IL-6) in response to treatments with bscCD19×CD3. IL-6 levels were determined by ELISA and are expressed as pg/ml. The time axis shows days (d) after the onset of first drug treatment and, starting with zero, hours (h) following the individual drug additions. Arrows indicate the time points of drug administration.

Figure 21:
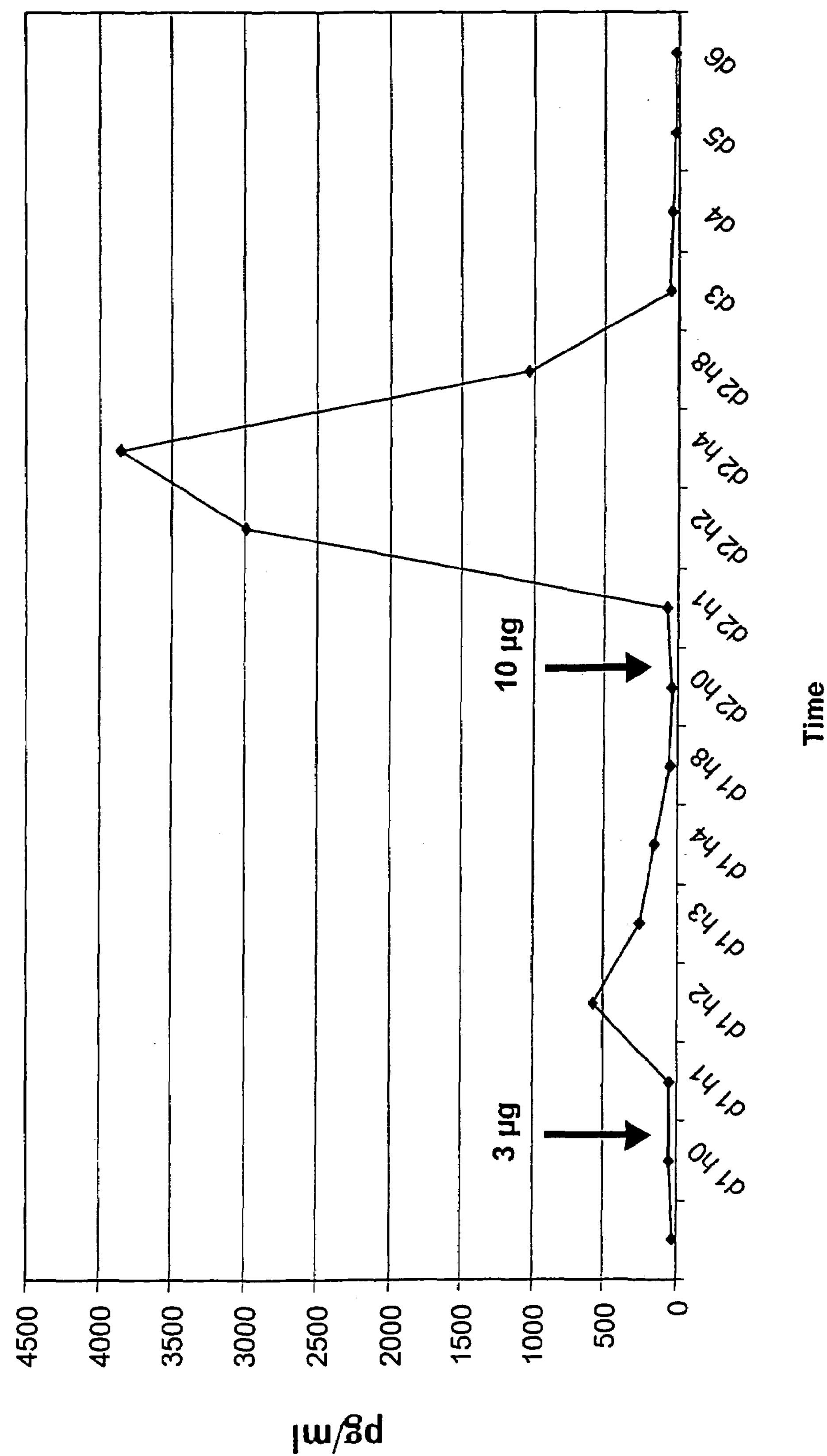

FIG. 21: Blood levels of interleukin-8 (IL-8) in response to treatments with bscCD19×CD3. IL-8 levels were determined by ELISA and are expressed as pg/ml. The time axis shows days (d) after the onset of first drug treatment and, starting with zero, hours (h) following the individual drug additions. Arrows indicate the time points of drug administration.

Figure 22:
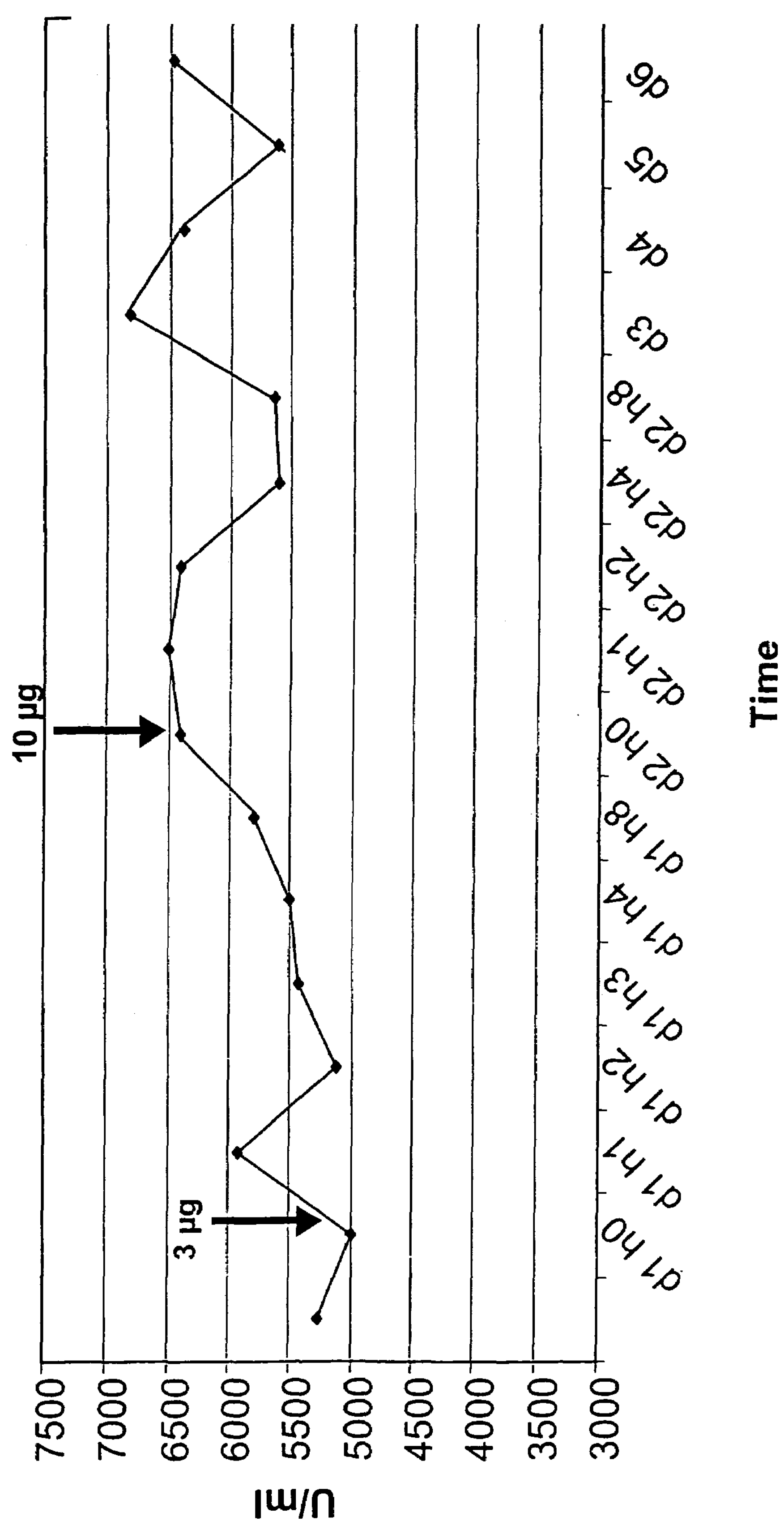

FIG. 22: Blood levels of soluble interleukin-2 receptor alpha-chain (IL-2R) in response to treatments with bscCD19×CD3. IL-2R levels were determined by ELISA and are expressed as Units/ml. The time axis shows days (d) after the onset of first drug treatment and, starting with zero, hours (h) following the individual drug additions. Arrows indicate the time points of drug administration.

DETAILED DESCRIPTION

The terms "first domain" and "second domain" in accordance with the present invention mean that one binding site is directed against the pan B cell marker CD19, which is uniformly expressed on the vast majority of malignant B cells, the other binding site is directed against the CD3 antigen of human T cells.

The term "binding site" as used in accordance with the present invention denotes a domain comprising a three-dimensional structure capable of specifically binding to an epitope like native antibodies, free scFv fragments or one of their corresponding immunoglobulin chains, preferably the $V_H$ chain. Thus, said domain can comprise the $V_H$ and/or $V_L$ domain of an antibody or an immunoglobulin chain, preferably at least the $V_H$ domain. On the other hand, said binding sites contained in the polypeptide of the invention may comprise at least one complementarity determining region (CDR) of an antibody or immunoglobulin chain recognizing the CD19 and CD3 antigens, respectively. In this respect, it is noted that the domains of the binding sites present in the polypeptide of the invention may not only be derived from antibodies but also from other CD19 or CD3 binding proteins, such as naturally occurring surface receptors or ligands. In accordance with the invention, said binding site is comprised in a domain.

The term "multifunctional polypeptide" as used herein denotes a polypeptide comprising at least two amino acid sequences derived from different origins, i.e. from two different molecules, optionally derived from different species wherein at least two of said origins specify the binding sites.

Accordingly, said binding sites specify the functions or at least some functions of said multifunctional peptide. Such polypeptides include, for example, bispecific single-chain (bsc) antibodies.

The term "single-chain" as used in accordance with the present invention means that said first and second domain of the polypeptide are covalently linked, preferably in the form of a co-linear amino acid sequence encodable by a nucleic acid molecule.

CD19 denotes an antigen that is expressed in the B lineage such as in the pro B cell and the mature B cell, it is not shed, is uniformly expressed on all lymphoma cells, and is absent from stem cells (8, 14).

CD3 denotes an antigen that is expressed on T-cells as part of the multimolecular T-cell receptor complex and that consists of three different chains CD3ϵ, CD3δ and CD3γ. Clustering of CD3 on T-cells, e.g., by immobilized anti-CD3-antibodies, leads to T-cell activation similar to the engagement of the T-cell receptor but independent from its clone typical specificity. Actually, most anti-CD3-antibodies recognize the CD3ϵ-chain.

Antibodies that specifically recognize CD19 or CD3 antigen are described in the prior art, e.g., in (24), (25) and (43), respectively, and can be generated by conventional methods known in the art.

Bispecific CD19×CD3 antibodies which are not of the single-chain format, retargeting T-cell cytotoxicity on lymphoma cells in a MHC-independent manner have already been shown to be effective in vitro (5, 6, 9-11, 13, 43), in animal models (7, 28) as well as in some pilot clinical trials (12, 29, 30). So far these antibodies were constructed by hybrid-hybridoma techniques, by covalently linking the monoclonal antibodies (31) or by diabody approach (43). More extensive clinical studies have been hampered by the fact that these antibodies have low biological activity such that high dosages have to be applied and that application of the antibodies alone did not provide for a beneficial therapeutic effect. Furthermore, the availability of clinical grade material was limited.

Without being bound to a particular theory, it is believed that using the bispecific antibody-like format as defined above, thus generated polypeptides such as bispecific CD19×CD3 antibodies are usually capable of destroying CD19-positive target cells by recruitment of cytotoxic T-lymphocytes without any need for T-cell pre- and/or co-stimulation. This is in sharp contrast to all known bispecific CD19×CD3 antibodies produced according to other molecular formats and usually does not depend on the particular CD19- or CD3-antibody specificities used to construct, e.g., the bispecific single-chain antibody. The independence from T-cell pre- and/or co-stimulation may substantially contribute to the exceptionally high cytotoxicity mediated by the polypeptide of the invention as exemplified by the particular CD19×CD3 bispecific antibody described in the examples.

A further advantageous property of the polypeptide of the invention is that due to its small, relatively compact structure it is easy to produce and purify, thereby circumventing the problems of low yields, occurrence of ill-defined by-products, or laborious purification procedures (15-19) reported for CD19×CD3 specific antibodies hitherto produced from hybrid-hybridomas, by chemical linkage or by renaturation from bacterial inclusion bodies. In the following, the advantageous and unexpected properties of the polypeptide of the invention will be discussed in a non-limiting manner guided by the appended examples, including some of the preferred embodiments of the invention referred to hereinbelow, which illustrate the broad concept of the present invention.

In accordance with the present invention, a eukaryotic expression system was used that had been developed for the production of recombinant bispecific single chain antibodies (1) in order to generate a recombinant bispecific CD19×CD3 single chain antibody by expression in CHO cells. The fully functional antibody was easily purified from the culture supernatant by its C-terminal histidine tag on a Ni-NTA chromatography column. Specific binding to CD19 and CD3 was demonstrated by FACS analysis. The resultant bscCD19×CD3 (bispecific single-chain CD19×CD3) molecule of the invention showed some unexpected properties:

it induced high lymphoma directed T cell cytotoxicity in vitro and in vivo. Even at very low concentrations of 10-100 pg/ml and low E (effector):T (target) ratios of 5:1 and 2.5:1 significant specific lysis of lymphoma cell lines was observed. Furthermore, 3 μg to 10 μg of the bscCD19×CD3 molecule of the invention in compassionate use showed clear and significant improvement of medical status. Compared to so far published CD19×CD3 antibodies produced by hybrid-hybridoma techniques or by diabody approaches (which also represent a different format) which show cytotoxic activity in the range of several nanograms/ml or even μg/ml, the bscCD19×CD3 antibody of the invention seems to be much more efficacious (5-7, 27, 43) as, e.g., documented in appended examples 4, 5 and 7; and even low concentrations of the bscCD19×CD3 of the invention were able to induce rapid lymphoma directed cytotoxicity (after 4 h) at low E:T ratios without the need of any T cell prestimulation. In contrast, a conventional CD19×CD3 bispecific antibody (5-7, 27) showed no significant cytotoxic activity under these conditions (namely no T cell prestimulation, low E:T ratio) even at high concentrations up to 3000 ng/ml. Although induction of cytotoxic activity without prestimulation has also been reported in the case of another conventional CD19×CD3 antibody this effect was achieved only at high concentrations and high E:T ratios (100 ng/ml, 27:1) (9) compared to the bscCD19×CD3 of the invention (100 pg/ml, 2.5:1). Moreover, a cytotoxic effect of this conventional antibody was observed only after 1 day of prestimulation with the bispecific antibody itself whereas the bscCD19×CD3 of the invention induced lymphoma-directed cytotoxicity already after 4 hours. To the knowledge of the inventors such rapid and specific cytotoxic activity of unstimulated T cells at such low concentrations and E:T ratios has not been described for other bispecific antibodies used so far. Although recently a anti-p185HER2/anti-CD3 bispecific $F(ab)_2$ antibody has been shown to induce cytotoxic activity at similar concentrations as the bscCD19×CD3 of the invention, this antibody required 24 hr prestimulation with IL-2 (32). Thus, the bscCD19×CD3 antibody of the invention reveals unique cytotoxic properties that discriminate this molecule from other bispecific antibodies that have been described.

The bscCD19×CD3 of the invention mediates cytotoxic effects that are antigen specific, demonstrated by the facts that this antibody failed to lyse the plasmacytoma cell lines NCl and L363 which are cell lines of the B lineage not expressing the CD19 antigen; and that the cytotoxicity against lymphoma cells could be blocked by the parental anti-CD19 antibody HD37. (HD37 antibody is derived from the HD37 hybridoma (22)).

Blocking the perforin-pathway by calcium-deprivation with EGTA completely blocked bscCD19×CD3-mediated cytotoxicity suggesting that specific lysis is a T cell-mediated effect rather than a direct effect of the antibody itself.

Taken together, the bscCD19×CD3 antibody constructed according to general teaching of the invention is superior to so far described CD19×CD3 bispecific antibodies with respect to its considerably higher biological activity as well as the possibility of its fast and easy production, thereby yielding sufficient amounts of high quality clinical grade material.

Therefore, the bscCD19×CD3 molecules of the invention are expected to be a suitable candidate to prove the therapeutic benefit of bispecific antibodies in the treatment of B-cell mediated diseases such as non-Hodgkin lymphoma in clinical trials.

In a preferred embodiment of the polypeptide of the invention said domains are connected by a polypeptide linker. Said linker is disposed between said first and said second domain, wherein said polypeptide linker preferably comprises plural, hydrophilic, peptide-bonded amino acids and connects the N-terminal end of said first domain and the C-terminal end of said second domain.

In a further preferred embodiment of the invention said first and/or second domain of the above-described polypeptide mimic or correspond to a $V_H$ and $V_L$ region from a natural antibody. The antibody providing the binding site for the polypeptide of the invention can be, e.g., a monoclonal antibody, polyclonal antibody, chimeric antibody, humanized antibody, bispecific antibody, synthetic antibody, antibody fragment, such as Fab, Fv or scFv fragments etc., or a chemically modified derivative of any of these. Monoclonal antibodies can be prepared, for example, by the techniques as originally described in Köhler and Milstein, *Nature* 256 (1975), 495, and Galfré, *Meth. Enzymol.* 73 (1981), 3, which comprise the fusion of mouse myeloma cells to spleen cells derived from immunized mammals with modifications developed by the art. Furthermore, antibodies or fragments thereof to the aforementioned antigens can be obtained by using methods which are described, e.g., in Harlow and Lane "Antibodies, A Laboratory Manual", CSH Press, Cold Spring Harbor, 1988. Antibodies might be obtained from several species, including human. When derivatives of said antibodies are obtained by the phage display technique, surface plasmon resonance as employed in the BIAcore system can be used to increase the efficiency of phage antibodies which bind to an epitope of the CD19 or CD3 antigen (Schier, *Human Antibodies Hybridomas* 7 (1996), 97-105; Malmborg, *J. Immunol. Methods* 183 (1995), 7-13). The production of chimeric antibodies is described, for example, in WO 89/09622. Methods for the production of humanized antibodies are described in, e.g., EP-A1 0 239 400 and WO 90/07861. A further source of antibodies to be utilized in accordance with the present invention are so-called xenogenic antibodies. The general principle for the production of xenogenic antibodies such as human antibodies in mice is described in, e.g., WO 91/10741, WO 94/02602, WO 96/34096 and WO 96/33735.

Antibodies to be employed in accordance with the invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning: A Laboratory Manual, Cold Spring Harbor Laboratory (1989) N.Y. The modification referred to are preferably carried out at the nucleic acid level.

In a further preferred embodiment of the invention at least one of said domains in the above-described polypeptide is a single-chain fragment of the variable region of the antibody.

As is well known, Fv, the minimum antibody fragment which contains a complete antigen recognition and binding site, consists of a dimer of one heavy and one light chain variable domain ($V_H$ and $V_L$) in non-covalent association. In this configuration that corresponds to the one found in native antibodies the three complementarity determining regions (CDRs) of each variable domain interact to define an antigen binding site on the surface of the $V_H$-$V_L$ dimer. Collectively, the six CDRs confer antigen binding specificity to the antibody. Frameworks (FRs) flanking the CDRs have a tertiary structure which is essentially conserved in native immunoglobulins of species as diverse as human and mouse. These FRs serve to hold the CDRs in their appropriate orientation. The constant domains are not required for binding function, but may aid in stabilizing $V_H$-$V_L$ interaction. Even a single variable domain (or half of an Fv comprising only three CDRs specific for an antigen) has the ability to recognize and bind antigen, although usually at a lower affinity than an entire binding site (Painter, Biochem. 11 (1972), 1327-1337). Hence, said domain of the binding site of the polypeptide of the invention can be a pair of $V_H$-$V_L$, $V_H$-$V_H$ or $V_L$-$V_L$ domains either of the same or of different immunoglobulins. The order of $V_H$ and $V_L$ domains within the polypeptide chain is not decisive for the present invention, the order of domains given hereinabove may be reversed usually without any loss of function. It is important, however, that the $V_H$ and $V_L$ domains are arranged so that the antigen binding site can properly fold.

In a preferred embodiment of the polypeptides of the invention said domains are arranged in the order $V_L$CD19-$V_H$CD19-$V_H$CD3-$V_L$CD3, wherein "$V_L$" and "$V_H$" means the light and heavy chain of the variable domain of specific anti-CD19 and anti-CD3 antibodies.

As discussed above, said binding sites are preferably connected by a flexible linker, preferably by a polypeptide linker disposed between said domains, wherein said polypeptide linker comprises plural, hydrophilic, peptide-bonded amino acids of a length sufficient to span the distance between the C-terminal end of one of said domains comprising said binding sites and the N-terminal end of the other of said domains comprising said binding sites when the polypeptide of the invention assumes a conformation suitable for binding when disposed in aqueous solution. Preferably, said polypeptide linker comprises a plurality of glycine, alanine and/or serine residues. It is further preferred that said polypeptide linker comprises a plurality of consecutive copies of an amino acid sequence. Usually, the polypeptide linker comprises 1 to 15 amino acids although polypeptide linkers of more than 15 amino acids may work as well. In a preferred embodiment of the invention said polypeptide linker comprises 1 to 5 amino acid residues.

In a particularly preferred embodiment of the present invention said polypeptide linker in the polypeptide of the invention comprises 5 amino acids. As demonstrated in the appended examples, said polypeptide linker advantageously comprises the amino acid sequence Gly Gly Gly Gly Ser (SEQ ID NO:11).

In a further particularly preferred embodiment, said first domain of the polypeptide of the invention comprises at least one CDR of the $V_H$ and $V_L$ region comprising the amino acid sequence encoded by the DNA sequence depicted in FIG. 8 from nucleotides 82 to 414 ($V_L$) and nucleotides 460 to 831 ($V_H$) and/or said second domain comprises at least one CDR, more preferred two, most preferred three CDRs of the $V_H$ and $V_L$ region comprising the amino acid sequence encoded by the DNA sequence depicted in FIG. 8 from nucleotides 847 to 1203 ($V_H$) and nucleotides 1258 to 1575 ($V_L$), optionally, in combination with framework regions that occur together with said CDRs in parental antibodies. The CDRs contained in the variable regions depicted in FIG. 8 can be determined, for example, according to Kabat, "Sequences of Proteins of Immunological Interest" (U.S. Department of Health and Human Services, third edition, 1983; fourth edition, 1987; fifth edition, 1990). The person skilled in the art will readily appreciate that the binding site or at least one CDR derived therefrom can be used for the construction of a polypeptide of the invention. Preferably, said polypeptide comprises the amino acid sequence encoded by the DNA sequence as depicted in FIG. 8 from nucleotides 82 to 1575. The person skilled in the art will readily appreciate that binding sites of the polypeptide of the invention can be constructed according to methods known in the art, e.g., as described in EP-A1 0 451 216 and EP-A1 0 549 581.

The domains of the binding sites of the polypeptide of the invention preferably have a specificity at least substantially identical to the binding specificity of the, e.g., antibody or immunoglobulin chain where they are derived from. Such binding site domains can have a binding affinity of at least $10^5 M^{-1}$, preferably not higher than $10^7 M^{-1}$ for the CD3 antigen and advantageously up to $10^{10} M^{-1}$ or higher for the CD19 antigen.

In a preferred embodiment of the polypeptide of the invention said binding site of the first domain has an affinity of at least about $10^7$M, preferably at least about $10^9$M and most preferably at least about $10^{-11}$ M; and/or said binding site of the second domain has an affinity of less than about $10^7$M, preferably less than about $10^6$M and most preferably in the order of $10^5$M.

In accordance with the preferred embodiments referred to above, it is advantageous if the binding site recognizing the CD19 antigen has a high affinity in order to capture the target cells to be destroyed with high efficiency. On the other hand, the binding affinity of the binding site recognizing the CD3 antigen should be in the order of those of the natural CD3 receptor or of that usually found for the interaction of the T-cell receptor with its ligand, that is an MHC-peptide complex on the target cell surface.

In another preferred embodiment of the invention, the polypeptide described above is a bispecific single-chain antibody.

The present invention further relates to a polypeptide comprising at least one further domain, said domains being linked by covalent or non-covalent bonds.

The linkage can be based on genetic fusion according to the methods known in the art and described above or can be performed by, e.g., chemical cross-linking as described in, e.g., WO 94/04686. The additional domain present in the polypeptide of the invention may preferably be linked by a flexible linker, advantageously a polypeptide linker to one of the binding site domains wherein said polypeptide linker comprises plural, hydrophilic, peptide-bonded amino acids of a length sufficient to span the distance between the C-terminal end of one of said domains and the N-terminal end of the other of said domains when said polypeptide assumes a conformation suitable for binding when disposed in aqueous solution. Preferably, said polypeptide linker is a polypeptide linker as described in the embodiments hereinbefore. The polypeptide of the invention may further comprise a cleavable linker or cleavage site for proteinases, such as enterokinase; see also the appended examples.

Furthermore, said additional domain may be of a predefined specificity or function. For example, the literature contains a host of references to the concept of targeting bioactive substances such as drugs, toxins, and enzymes to specific points in the body to destroy or locate malignant cells or to induce a localized drug or enzymatic effect. It has been proposed to achieve this effect by conjugating the bioactive substance to monoclonal antibodies (see, e.g., N.Y. Oxford University Press; and Ghose, J. Natl. Cancer Inst. 61 (1978), 657-676).

In this context, it is also understood that the polypeptides according to the invention may be further modified by conventional methods known in the art. This allows for the construction of chimeric proteins comprising the polypeptide of the invention and other functional amino acid sequences, e.g., nuclear localization signals, transactivating domains, DNA-binding domains, hormone-binding domains, protein tags (GST, GFP, h-myc peptide, FLAG, HA peptide) which may be derived from heterologous proteins. As described in the appended examples, the polypeptide of the invention preferably comprises a FLAG-tag of about 8 amino acids in length; see FIG. 8.

The polypeptides of the invention can be used therapeutically in patients suffering from B-cell disorders such as B-cell lymphoma, B-cell derived chronic lymphatic leukemia (B-CLL) and/or having a B-cell related autoimmune disease such as myasthenia gravis, Morbus Basedow, Hashimoto thyreoiditis, or Goodpasture syndrome. Such therapy can be accomplished by, for example, the administration of polypeptides of the invention. Such administration can utilize unlabeled as well as labeled polypeptides.

For example, the polypeptides of the invention could be administered labeled with a therapeutic agent. These agents can be coupled either directly or indirectly to the antibodies or antigens of the invention. One example of indirect coupling is by use of a spacer moiety. These spacer moieties, in turn, can be either insoluble or soluble (Diener, Science 231 (1986), 148) and can be selected to enable drug release from the antigen at the target site. Examples of therapeutic agents which can be coupled to the polypeptides of the invention for immunotherapy are drugs, radioisotopes, lectins, and toxins. The drugs which can be conjugated to the polypeptides of the invention include compounds which are classically referred to as drugs such as mitomycin C, daunorubicin, and vinblastine.

In using radioisotopically conjugated polypeptides of the invention for, e.g., immunotherapy, certain isotopes may be more preferable than others depending on such factors as leukocyte distribution as well as stability and emission. Depending on the autoimmune response, some emitters may be preferable to others. In general, $\alpha$ and $\beta$ particle-emitting radioisotopes are preferred in immunotherapy. Preferred are short rage, high energy $\alpha$ emitters such as $^{212}$Bi. Examples of radioisotopes which can be bound to the polypeptides of the invention for therapeutic purposes are $^{125}$I, $^{131}$I, $^{90}$Y, $^{67}$Cu, $^{212}$Bi, $^{212}$At, $^{211}$Pb, $^{47}$Sc, $^{109}$Pd and $^{188}$Re.

Lectins are proteins, usually isolated from plant material, which bind to specific sugar moieties. Many lectins are also able to agglutinate cells and stimulate lymphocytes. However ricin is a toxic lectin which has been used immunotherapeutically. This is accomplished by binding the $\alpha$-peptide chain of ricin, which is responsible for toxicity, to the polypeptide to enable site specific delivery of the toxic effect.

Toxins are poisonous substances produced by plants, animals, or microorganisms that, in sufficient dose, are often lethal. Diphtheria toxin is a substance produced by *Corynebacterium* diphtheria which can be used therapeutically. This toxin consists of an $\alpha$ and $\beta$ subunit which under proper conditions can be separated. The toxic A component can be bound to a polypeptide of the invention and be used for site specific delivery to the interacting B-cell and T-cell which have brought into close proximity by a binding to a polypeptide of the invention.

Other therapeutic agents such as described above which can be coupled to the polypeptide of the invention, as well as corresponding ex vivo and in vivo therapeutic protocols, are known, or can be easily ascertained, by those of ordinary skill in the art. Wherever appropriate the person skilled in the art may use a polynucleotide of the invention described hereinbelow encoding any one of the above described polypeptides or the corresponding vectors instead of the proteinaceous material itself.

Thus, the person skilled in the art will readily appreciate that the polypeptide of the invention can be used for the construction of other polypeptides of desired specificity and biological function. The polypeptides of the invention are expected to play an important therapeutic and scientific role in particular in the medical field, for example, in the development of new treatment approaches for B-cell related disorders such as certain forms of cancer and autoimmune diseases or as interesting tools for the analysis and modulation of the corresponding cellular signal transduction pathways.

In a further preferred embodiment of the invention, said at least one further domain comprises a molecule selected from the group consisting of effector molecules having a conformation suitable for biological activity, amino acid sequences capable of sequestering an ion, and amino acid sequences capable of selective binding to a solid support or to a preselected antigen.

Preferably, said further domain comprises an enzyme, toxin, receptor, binding site, biosynthetic antibody binding site, growth factor, cell-differentiation factor, lymphokine, cytokine, hormone, a remotely detectable moiety, anti-metabolite, a radioactive atom or an antigen. Said antigen can be, e.g., a tumor antigen, a viral antigen, a microbial antigen, an allergen, an auto-antigen, a virus, a microorganism, a polypeptide, a peptide or a plurality of tumor cells.

Furthermore, said sequence capable of sequestering an ion is preferably selected from calmodulin, methallothionein, a functional fragment thereof, or an amino acid sequence rich in at least one of glutamic acid, asparatic acid, lysine, and arginine.

In addition, said polypeptide sequence capable of selective binding to a solid support can be a positively or a negatively charged amino acid sequence, a cysteine-containing amino acid sequence, avidin, streptavidin, a functional fragment of *Staphylococcus* protein A, GST, a His-tag, a FLAG-tag or Lex A. As is described in the appended Examples, the polypeptide of the invention exemplified by a single-chain antibody has also been expressed with an N-terminal FLAG-tag and/or C-terminal His-tag that allow for easy purification and detection. The FLAG-tag used in the example comprises 8 amino acids (see FIG. 8) and is thus preferably used in accordance with the present invention. However, FLAG-tags comprised of shortened versions of the FLAG used in the appended examples such as the amino acid sequence Asp-Tyr-Lys-Asp (SEQ ID NO:12) are suitable as well.

The effector molecules and amino acid sequences described above may be present in a proform which itself is either active or not and which may be removed, when, e.g., entering a certain cellular environment.

In a most preferred embodiment of the invention, said receptor is a costimulatory surface molecule important for T-cell activation or comprises an epitope binding site or a hormone binding site.

In a further most preferred embodiment of the invention, said costimulatory surface molecule is CD80 (B7-1) or CD86 (B7-2).

Yet, in a further embodiment, the present invention relates to polynucleotides which upon expression encode the above-described polypeptides. Said polynucleotides may be fused to suitable expression control sequences known in the art to ensure proper transcription and translation of the polypeptide.

Said polynucleotide may be, e.g., DNA, cDNA, RNA or synthetically produced DNA or RNA or a recombinantly produced chimeric nucleic acid molecule comprising any of those polynucleotides either alone or in combination. Preferably said polynucleotide is part of a vector. Such vectors may comprise further genes such as marker genes which allow for the selection of said vector in a suitable host cell and under suitable conditions. Preferably, the polynucleotide of the invention is operatively linked to expression control sequences allowing expression in prokaryotic or eukaryotic cells. Expression of said polynucleotide comprises transcription of the polynucleotide into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers, and/or naturally-associated or heterologous promoter regions. Possible regulatory elements permitting expression in prokaryotic host cells comprise, e.g., the PL, lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the polynucleotide. Furthermore, depending on the expression system used leader sequences capable of directing the polypeptide to a cellular compartment or secreting it into the medium may be added to the coding sequence of the polynucleotide of the invention and are well known in the art; see also, e.g., the appended examples. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including an N-terminal identification peptide imparting desired characteristics, e.g., stabilization or simplified purification of expressed recombinant product; see supra. In this context, suitable expression vectors are known in the art such as Okayama-Berg cDNA expression vector pcDV1 (Pharmacia), pCDM8, pRc/CMV, pcDNA1, pcDNA3 (Invitrogene), or pSPORT1 (GIBCO BRL).

Preferably, the expression control sequences will be eukaryotic promoter systems in vectors capable of transforming of transfecting eukaryotic host cells, but control sequences for prokaryotic hosts may also be used. Once the vector has been incorporated into the appropriate host, the host is maintained under conditions suitable for high level expression of the nucleotide sequences, and as desired, the collection and purification of the polypeptide of the invention may follow; see, e.g., the appended examples.

As described above, the polynucleotide of the invention can be used alone or as part of a vector to express the polypeptide of the invention in cells, for, e.g., gene therapy or diagnostics of diseases related to B-cell disorders. The polynucleotides or vectors containing the DNA sequence(s) encoding any one of the above described polypeptides is introduced into the cells which in turn produce the polypeptide of interest. Gene therapy, which is based on introducing therapeutic genes into cells by ex-vivo or in-vivo techniques is one of the most important applications of gene transfer. Suitable vectors, methods or gene-delivery systems for in-vitro or in-vivo gene therapy are described in the literature and are known to the person skilled in the art; see, e.g., Giordano, *Nature Medicine* 2 (1996), 534-539; Schaper, *Circ. Res.* 79 (1996), 911-919; Anderson, *Science* 256 (1992), 808-813; Verma, *Nature* 389 (1994), 239; Isner, *Lancet* 348 (1996), 370-374; Muhlhauser, *Circ. Res.* 77 (1995), 1077-1086; Onodera, *Blood* 91 (1998), 30-36; Verma, *Gene Ther.* 5 (1998), 692-699; Nabel, *Ann. N.Y. Acad. Sci.* 811 (1997), 289-292; Verzeletti, *Hum. Gene Ther.* 9 (1998), 2243-51; Wang, *Nature Medicine* 2 (1996), 714-716; WO 94/29469; WO 97/00957, U.S. Pat. No. 5,580,859; U.S. Pat. No. 5,589,466; or Schaper, *Current Opinion in Biotechnology* 7 (1996), 635-640, and references cited therein. The polynucleotides and vectors of the invention may be designed for direct introduction or for introduction via liposomes, or viral vectors (e.g., adenoviral, retroviral) into the cell. Preferably, said cell is a germ line cell, embryonic cell, or egg cell or derived therefrom, most preferably said cell is a stem cell. An example for an embryonic stem cell can be, inter alia, a stem cell as described in, Nagy, *Proc. Natl. Acad. Sci. USA* 90 (1993), 8424-8428.

In accordance with the above, the present invention relates to vectors, particularly plasmids, cosmids, viruses and bacteriophages used conventionally in genetic engineering that comprise a polynucleotide encoding a polypeptide of the invention. Preferably, said vector is an expression vector and/or a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell populations. Methods which are well known to those skilled in the art can be used to construct recombinant vectors; see, for example, the techniques described in Sambrook, *Molecular Cloning: A Laboratory Manual*, Cold Spring Harbor Laboratory (1989) N.Y. and Ausubel, *Current Protocols in Molecular Biology*, Green Publishing Associates and Wiley Interscience, N.Y. (1989). Alternatively, the polynucleotides and vectors of the invention can be reconstituted into liposomes for delivery to target cells. The vectors containing the polynucleotides of the invention can be transferred into the host cell by well-known methods, which vary depending on the type of cellular host. For example, calcium chloride transfection is commonly utilized for prokaryotic cells, whereas calcium phosphate treatment or electroporation may be used for other cellular hosts; see Sambrook, supra. Once expressed, the polypeptides of the present invention can be purified according to standard procedures of the art, including ammonium sulfate precipitation, affinity columns, column chromatography, gel electrophoresis and the like; see, Scopes, "Protein Purification", Springer-Verlag, N.Y. (1982). Substantially pure polypeptides of at least about 90 to 95% homogeneity are preferred, and 98 to 99% or more homogeneity are most preferred, for pharmaceutical uses. Once purified, partially or to homogeneity as desired, the polypeptides may then be used therapeutically (including extracorporeally) or in developing and performing assay procedures.

In a still further embodiment, the present invention relates to a cell containing the polynucleotide or vector described above. Preferably, said cell is a eukaryotic, most preferably a mammalian cell if therapeutic uses of the polypeptide are envisaged. Of course, yeast and less preferred prokaryotic, e.g., bacterial cells may serve as well, in particular if the produced polypeptide is used as a diagnostic means.

The polynucleotide or vector of the invention which is present in the host cell may either be integrated into the genome of the host cell or it may be maintained extrachromosomally.

The term "prokaryotic" is meant to include all bacteria which can be transformed or transfected with a DNA or RNA molecules for the expression of a polypeptide of the invention. Prokaryotic hosts may include gram negative as well as gram positive bacteria such as, for example, *E. coli, S. typhimurium, Serratia marcescens* and *Bacillus subtilis*. The term "eukaryotic" is meant to include yeast, higher plant, insect and preferably mammalian cells. Depending upon the host employed in a recombinant production procedure, the polypeptides of the present invention may be glycosylated or may be non-glycosylated. Polypeptides of the invention may also include an initial methionine amino acid residue. A polynucleotide coding for a polypeptide of the invention can be used to transform or transfect the host using any of the techniques commonly known to those of ordinary skill in the art. Especially preferred is the use of a plasmid or a virus containing the coding sequence of the polypeptide of the invention and genetically fused thereto an N-terminal FLAG-tag and/or C-terminal His-tag. Preferably, the length of said FLAG-tag is about 4 to 8 amino acids, most preferably 8 amino acids. Methods for preparing fused, operably linked genes and expressing them in, e.g., mammalian cells and bacteria are well-known in the art (Sambrook, *Molecular Cloning: A Laboratory Manual*, Cold Spring Harbor Laboratory, Cold Spring Harbor, N.Y., 1989). The genetic constructs and methods described therein can be utilized for expression of the polypeptide of the invention in eukaryotic or prokaryotic hosts. In general, expression vectors containing promoter sequences which facilitate the efficient transcription of the inserted polynucleotide are used in connection with the host. The expression vector typically contains an origin of replication, a promoter, and a terminator, as well as specific genes which are capable of providing phenotypic selection of the transformed cells. Furthermore, transgenic animals, preferably mammals, comprising cells of the invention may be used for the large scale production of the polypeptide of the invention.

In a further embodiment, the present invention thus relates to a process for the preparation of a polypeptide described above comprising cultivating a cell of the invention under conditions suitable for the expression of the polypeptide and isolating the polypeptide from the cell or the culture medium.

The transformed hosts can be grown in fermentors and cultured according to techniques known in the art to achieve optimal cell growth. The polypeptide of the invention can then be isolated from the growth medium, cellular lysates, or cellular membrane fractions. The isolation and purification of the, e.g., microbially expressed polypeptides of the invention may be by any conventional means such as, for example, preparative chromatographic separations and immunological separations such as those involving the use of monoclonal or polyclonal antibodies directed, e.g., against a tag of the polypeptide of the invention or as described in the appended examples.

Thus, the present invention allows the recombinant production of polypeptides comprising binding sites having affinity and specificity for an epitope of the CD19 and CD3 antigen, respectively, and optionally a further functional domain. As is evident from the foregoing, the invention provides a large family of polypeptides comprising such binding sites for any use in therapeutic and diagnostic approaches. It will be apparent to those skilled in the art that the polypeptides of the invention can be further coupled to other moieties as described above for, e.g., drug targeting and imaging applications. Such coupling may be conducted chemically after expression of the polypeptides to site of attachment or the coupling product may be engineered into the polypeptide of the invention at the DNA level. The DNAs are then expressed in a suitable host system, and the expressed proteins are collected and renatured, if necessary. As described above, the binding sites are preferably derived from the variable region of antibodies. In this respect, hybridoma technology enables production of cell lines secreting antibody to essentially any desired substance that produces an immune response. RNA encoding the light and heavy chains of the immunoglobulin can then be obtained from the cytoplasm of the hybridoma. The 5' end portion of the mRNA can be used to prepare cDNA to be used in the method of the present invention. The DNA encoding the polypeptides of the invention can subsequently be expressed in cells, preferably mammalian cells.

Depending on the host cell, renaturation techniques may be required to attain proper conformation. If necessary, point substitutions seeking to optimize binding may be made in the DNA using conventional cassette mutagenesis or other protein engineering methodology such as is disclosed herein. Preparation of the polypeptides of the invention may also be dependent on knowledge of the amino acid sequence (or corresponding DNA or RNA sequence) of bioactive proteins such as enzymes, toxins, growth factors, cell differentiation factors, receptors, anti-metabolites, hormones or various cytokines or lymphokines. Such sequences are reported in the literature and available through computerized data banks. For example, a polypeptide of the invention can be constructed that, e.g., consists of the single-chain Fv fragment and the extracellular part of the human costimulatory protein CD80 (B7-1) connected by a (Gly4Ser1)1 linker. The CD80 costimulatory protein belongs to the Ig superfamily. It is a heavily glycosylated protein of 262 amino acids. A more detailed description was published by Freeman, *J. Immunol.* 143 (1989), 2714-2722. Stable expression can be performed in, e.g., DHFR deficient CHO-cells as described by Kaufmann, *Methods Enzymol.* 185 (1990), 537-566. The protein can then be purified via its His-tag attached to the C-terminus by using a Ni-NTA-column (Mack, *Proc. Natl. Acad. Sci. U.S.A.* 92 (1995), 7021-7025).

Additionally, the present invention provides for compositions comprising the aforementioned polypeptide, the polynucleotide or the vector of the invention.

Preferably, the present invention relates to compositions which are pharmaceutical compositions comprising these aforementioned polypeptide(s), polynucleotide(s) or vector(s) of the invention.

The pharmaceutical composition of the present invention may further comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical or intradermal administration. The dosage regiment will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Generally, the regimen as a regular administration of the pharmaceutical composition should be in the range of 1 μg to 10 mg units per day. If the regimen is a continuous infusion, it should also be in the range of 1 μg to 10 mg units per kilogram of body weight per minute, respectively. However, a more preferred dosage for continuous infusion might be in the range of 0.01 μg to 10 mg units per kilogram of body weight per hour. Particularly preferred dosages are recited herein below. Progress can be monitored by periodic assessment. Dosages will vary but a preferred dosage for intravenous administration of DNA is from approximately $10^6$ to $10^{12}$ copies of the DNA molecule. The compositions of the invention may be administered locally or systematically. Administration will generally be parenterally, e.g., intravenously; DNA may also be administered directed to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishes, electrolyte replenishers (such as those based on Ringer's dextrose), and the like. Preservatives and other additives may also be present such as, for example, antimicrobials, antioxidants, chelating agents, and inert gases and the like. In addition, the pharmaceutical composition of the present invention might comprise proteinaceous carriers, like, e.g., serum albumine or immunoglobuline, preferably of human origin. Furthermore, it is envisaged that the pharmaceutical composition of the invention might comprise further biologically active agents, depending on the intended use of the pharmaceutical composition. Such agents might be drugs acting on the gastro-intestinal system, drugs acting as cytostatica, drugs preventing hyperurikemia and/or agents such as T-cell co-stimulatory molecules or cytokines known in the art.

It is envisaged by the present invention that the various polynucleotides and vectors of the invention are administered either alone or in any combination using standard vectors and/or gene delivery systems, and optionally together with a pharmaceutically acceptable carrier or excipient. Subsequent to administration, said polynucleotides or vectors may be stably integrated into the genome of the subject.

On the other hand, viral vectors may be used which are specific for certain cells or tissues and persist in said cells. Suitable pharmaceutical carriers and excipients are well known in the art. The pharmaceutical compositions prepared according to the invention can be used for the prevention or treatment or delaying of different kinds of diseases, which are related to B-cell related immunodeficiencies and malignancies.

Furthermore, it is possible to use a pharmaceutical composition of the invention which comprises polynucleotide or vector of the invention in gene therapy. Suitable gene delivery systems may include liposomes, receptor-mediated delivery systems, naked DNA, and viral vectors such as herpes viruses, retroviruses, adenoviruses, and adeno-associated viruses, among others. Delivery of nucleic acids to a specific site in the body for gene therapy may also be accomplished using a biolistic delivery system, such as that described by Williams (*Proc. Natl. Acad. Sci. USA* 88 (1991), 2726-2729). Further methods for the delivery of nucleic acids comprise particle-mediated gene transfer as, e.g., described in Verma, *Gene Ther.* 15 (1998), 692-699.

It is to be understood that the introduced polynucleotides and vectors express the gene product after introduction into said cell and preferably remain in this status during the lifetime of said cell. For example, cell lines which stably express the polynucleotide under the control of appropriate regulatory sequences may be engineered according to methods well known to those skilled in the art. Rather than using expression vectors which contain viral origins of replication, host cells can be transformed with the polynucleotide of the invention and a selectable marker, either on the same or separate plasmids. Following the introduction of foreign DNA, engineered cells may be allowed to grow for 1-2 days in an enriched media, and then are switched to a selective media. The selectable marker in the recombinant plasmid confers resistance to the selection and allows for the selection of cells having stably integrated the plasmid into their chromosomes and grow to form foci which in turn can be cloned and expanded into cell lines. Such engineered cell lines are also particularly useful in screening methods for the detection of compounds involved in, e.g., B-cell/T-cell interaction.

A number of selection systems may be used, including but not limited to, the herpes simplex virus thymidine kinase (Wigler, *Cell* 11 (1977), 223), hypoxanthine-guanine phosphoribosyltransferase (Szybalska, *Proc. Natl. Acad. Sci. USA* 48 (1962), 2026), and adenine phosphoribosyltransferase (Lowy, *Cell* 22 (1980), 817) in tk-, hgprt- or Aprt-cells, respectively. Also, antimetabolite resistance can be used as the basis of selection for dhfr, which confers resistance to methotrexate (Wigler, *Proc. Natl. Acad. Sci. USA* 77 (1980), 3567; O'Hare, *Proc. Natl. Acad. Sci. USA* 78 (1981), 1527), gpt, which confers resistance to mycophenolic acid (Mulligan, *Proc. Natl. Acad. Sci. USA* 78 (1981), 2072); neo, which confers resistance to the aminoglycoside G-418 (Colberre-Garapin, *J. Mol. Biol.* 150 (1981), 1); hygro, which confers resistance to hygromycin (Santerre, *Gene* 30 (1984), 147); or puromycin (pat, puromycin N-acetyl transferase). Additional selectable genes have been described, for example, trpB, which allows cells to utilize indole in place of tryptophan, hisD, which allows cells to utilize histinol in place of histidine (Hartman, *Proc. Natl. Acad. Sci. USA* 85 (1988), 8047); and ODC (ornithine decarboxylase) which confers resistance to the ornithine decarboxylase inhibitor, 2-(difluoromethyl)-DL-ornithine, DFMO (McCologue, 1987, In: *Current Communications in Molecular Biology*, Cold Spring Harbor Laboratory ed.).

In another embodiment the present invention relates to a diagnostic composition comprising any one of the above described polypeptides, polynucleotides or vectors of the invention and optionally suitable means for detection.

The polypeptides of the invention are also suited for use in immunoassays in which they can be utilized in liquid phase or bound to a solid phase carrier. Examples of immunoassays which can utilize the polypeptide of the invention are competitive and non-competitive immunoassays in either a direct or indirect format. Examples of such immunoassays are the radioimmunoassay (RIA), the sandwich (immunometric assay) and the Western blot assay.

The polypeptides of the invention can be bound to many different carriers and used to isolate cells specifically bound to said polypeptides. Examples of well-known carriers include glass, polystyrene, polyvinyl chloride, polypropylene, polyethylene, polycarbonate, dextran, nylon, amyloses, natural and modified celluloses, colloidal metals, polyacrylamides, agaroses, and magnetite. The nature of the carrier can be either soluble or insoluble for the purposes of the invention.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds; see also the embodiments discussed hereinabove.

The present invention also relates to the use of the polypeptide, polynucleotide and vector of the invention described hereinabove for the preparation of a pharmaceutical composition for the treatment of B-cell malignancies, B-cell mediated autoimmune diseases or the depletion of B-cells.

Recent clinical studies with retargeted cytotoxic activity of human T cells by bispecific antibodies have shown promising results in the treatment of refractory Hodgkin's disease (33), breast and ovarian cancer (34-37) and malignant glioma (38). Given the facts that bsc antibodies due to their low molecular mass facilitate penetration into tumors (as has been shown for Fab or Fv fragments) (39); and that bsc antibodies are suspected to decrease the dose dependent and dose limiting toxicity caused by the systemic cytokine release mediated by the Fc parts of conventional bispecific antibodies (40); and that even an intact monoclonal antibody (directed against CD20) led to tumor regression in advanced stages of NHL (41, 42), it is expected—and has in fact been demonstrated—that the polypeptides of the invention are interesting molecules that contribute to further therapeutic improvements.

Thus, in a preferred embodiment the pharmaceutical composition of the invention is used for the treatment of non-Hodgkin lymphoma.

The dosage ranges of the administration of the polypeptides, polynucleotides and vectors of the invention are those large enough to produce the desired effect in which the symptoms of the B-cell mediated diseases are ameliorated. The dosage should not be so large as to cause essential adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. It is envisaged that the range of said dose is set at, e.g., 0.01 μg to 10 mg of the polypeptide of the invention. A particularly preferred dosage is 0.1 μg to 1 mg, even more preferred is 1 μg to 100 μg and most preferred is a dosage of 3 μg to 10 μg as, e.g., illustrated in appended example 7.

Furthermore, the invention relates to a method for identifying T-cell activating or co-stimulating compounds or for identifying inhibitors of T-cell activation and stimulation comprising culturing CD19 positive cells (preferably B-cells) and T-cells in the presence of the polypeptide of the invention and, optionally, in the presence of a component capable of providing a detectable signal in response to T-cell activation with a compound to be screened under conditions permitting interaction of the compound with the cells; and detecting the presence or absence of a signal generated from the interaction of the compound with the cells.

This embodiment is particularly useful for testing the capacity of compounds as co-stimulatory molecules. In this method, the CD19 positive cell/B-cell provides a primary activation signal for the T-cell, thus avoiding the clonotypic T-cell receptor. Then, it may be determined in accordance with the invention which compound to be tested is still necessary to actually activate the T-cell. In the method of the invention, the CD19 positive cell/B-cell functions as a stimulating cell that links bispecific molecules which are bound to CD3 complexes on the surface of the same T-cell. The biological methods for carrying out the culturing, detecting and, optionally, testing are clear to a person skilled in the art.

The term "compound" in the method of the invention includes a single substance or a plurality of substances which may or may not be identical.

Said compound(s) may be comprised in, for example, samples, e.g., cell extracts from, e.g., plants, animals or microorganisms. Furthermore, said compounds may be known in the art but hitherto not known to be capable of inhibiting T-cell activation or not known to be useful as a T-cell co-stimulatory factor, respectively. The plurality of compounds may be, e.g., added to the culture medium or injected into the cell.

If a sample containing (a) compound(s) is identified in the method of the invention, then it is either possible to isolate the compound from the original sample identified as containing the compound in question, or one can further subdivide the original sample, for example, if it consists of a plurality of different compounds, so as to reduce the number of different substances per sample and repeat the method with the subdivisions of the original sample. It can then be determined whether said sample or compound displays the desired properties by methods known in the art such as described herein and in the appended examples. Depending on the complexity of the samples, the steps described above can be performed several times, preferably until the sample identified according to the method of the invention only comprises a limited number of or only one substance(s). Preferably said sample comprises substances or similar chemical and/or physical properties, and most preferably said substances are identical. The methods of the present invention can be easily performed and designed by the person skilled in the art, for example, in accordance with other cell based assays described in the prior art or by using and modifying the methods as described in the appended examples. Furthermore, the person skilled in the art will readily recognize which further compounds and/or cells may be used in order to perform the methods of the invention, for example, interleukins, or enzymes, if necessary, that convert a certain compound into the precursor which in turn stimulates or suppresses T-cell activation. Such adaptation of the method of the invention is well within the skill of the person skilled in the art and can be performed without undue experimentation.

Compounds which can be used in accordance with the method of the present invention include peptides, proteins, nucleic acids, antibodies, small organic compounds, ligands, peptidomimetics, PNAs and the like. Said compounds can also be functional derivatives or analogues of known T-cell activators or inhibitors. Methods for the preparation of chemical derivatives and analogues are well known to those skilled in the art and are described in, for example, Beilstein, *Handbook of Organic Chemistry*, Springer edition New York Inc., 175 Fifth Avenue, New York, N.Y. 10010 U.S.A. and *Organic Synthesis*, Wiley, N.Y., USA. Furthermore, said derivatives and analogues can be tested for their effects according to methods known in the art or as described, for example, in the appended examples. Furthermore, peptidomimetics and/or computer aided design of appropriate activators or inhibitors of T-cell activation can be used, for example, according to the methods described below. Appropriate computer programs can be used for the identification of interactive sites of a putative inhibitor and the antigen of the invention by computer assistant searches for complementary structural motifs (Fassina, *Immunomethods* 5 (1994), 114-120). Further appropriate computer systems for the computer aided design of protein and peptides are described in the prior art, for example, in Berry, *Biochem. Soc. Trans.* 22 (1994), 1033-1036; Wodak, *Ann. N.Y. Acad. Sci.* 501 (1987), 1-13; Pabo, *Biochemistry* 25 (1986), 5987-5991. The results obtained from the above-described computer analysis can be used in combination with the method of the invention for, e.g., optimizing known T-cell activators or inhibitors. Appropriate peptidomimetics can also be identified by the synthesis of peptidomimetic combinatorial libraries through successive chemical modification and testing the resulting compounds, e.g., according to the method described herein and in the appended examples. Methods for the generation and use of peptidomimetic combinatorial libraries are described in the prior art, for example, in Ostresh, *Methods in Enzymology* 267 (1996), 220-234 and Dorner, *Bioorg. Med. Chem.* 4 (1996), 709-715. Furthermore, the three-dimensional and/or crystallographic structure of inhibitors or activators of B-cell/T-cell interaction can be used for the design of peptidomimetic inhibitors or activators of T-cell activation to be tested in the method of the invention (Rose, Biochemistry 35 (1996), 12933-12944; Rutenber, *Bioorg. Med. Chem.* 4 (1996), 1545-1558).

In summary, the present invention provides methods for identifying compounds which are capable of modulating B-cell/T-cell mediated immune responses.

Compounds found to activate B-cell/T-cell mediated responses may be used in the treatment of cancer and related diseases. In addition, it may also be possible to specifically inhibit viral diseases, thereby preventing viral infection or viral spread. Compounds identified as suppressors of T-cell activation or stimulation may be used in organ transplantation in order to avoid graft rejection; see also supra.

The compounds identified or obtained according to the method of the present invention are thus expected to be very useful in diagnostic and in particular for therapeutic applications. Hence, in a further embodiment the invention relates to a method for the production of a pharmaceutical composition comprising formulating the compound identified in step (b) of the above described methods of the invention in a pharmaceutically acceptable form. Furthermore, it is envisaged that said component might be modified by peptidomimetics. Methods for the generation and use of peptidomimetic combinatorial libraries are described in the prior art, for example Ostresh, *Methods in Enzymology* 267 (1996), 210-234, Dorner, *Bioorg. Med. Chem.* 4 (1996), 709-715, Beeley, *Trends Biotechnol.* 12 (1994), 213-216, or al-Obeidi, *Mol. Biotech.* 9 (1998), 205-223.

The therapeutically useful compounds identified according to the method of the invention may be administered to a patient by any appropriate method for the particular compound, e.g., orally, intravenously, parenterally, transdermally, transmucosally, or by surgery or implantation (e.g., with the compound being in the form of a solid or semi-solid biologically compatible and resorbable matrix) at or near the site where the effect of the compound is desired. Therapeutic doses are determined to be appropriate by one skilled in the art, see supra.

Additionally, the present invention provides for a method for the treatment of B-cell malignancies, B-cell mediated autoimmune diseases or the depletion of B-cells and/or for a method delaying a pathological condition which is caused by B-cell disorders comprising introducing the polypeptide, the polynucleotide or the vector of the invention into a mammal affected by said malignancies, disease and/or pathological condition. It is furthermore preferred that said mammal is a human.

These and other embodiments are disclosed and encompassed by the description and Examples of the present invention. Further literature concerning any one of the antibodies, methods, uses and compounds to be employed in accordance with the present invention may be retrieved from public libraries and databases, using for example electronic devices. For example, the public database "Medline" may be utilized which is available on the Internet. Further databases are known to the person skilled in the art. An overview of patent information in biotechnology and a survey of relevant sources of patent information useful for retrospective searching and for current awareness is given in Berks, TIBTECH 12 (1994), 352-364.

EXAMPLES

The invention will now be described by reference to the following biological examples which are merely illustrative and are not to be construed as a limitation of scope of the present invention.

Example 1

Cloning of Variable (V) Immunoglobulin Domains

The V light-chain ($V_L$) and V heavy chain ($V_H$) domains from the HD37 hybridoma (22) were cloned according to standard PCR methods (23). cDNA synthesis was carried out with oligo dT primers and Taq polymerase.

List of Primers

5'L1: [SEQ ID NO:1]

GAAGCACGCGTAGATATCKTGMTSACCCAAWCTCCA

3'K: [SEQ ID NO:2]

GAAGATGGATCCAGCGGCCGCAGCATCAGC

5'H1: [SEQ ID NO:3]

CAGCCGGCCATGGCGCAGGTSCAGCTGCAGSAG

3'G: [SEQ ID NO:4]

ACCAGGGGCCAGTGGATAGACAAGCTTGGGTGTCGTTTT

5'$V_L$B5RRV: [SEQ ID NO:5]

AGGTGTACACTCCATATCCAGCTGACCCAGTCTCCA

3'$V_L$GS15: [SEQ ID NO:6]

GGAGCCGCCGCCGCCAGAACCACCACCTTTGATCTCGAGCTTGGTCCC

5'$V_H$GS15: [SEQ ID NO:7]

GGCGGCGGCGGCTCCGGTGGTGGTGGTTCTCAGGTSMARCTGCAGSAG TCWGG

3'$V_H$BspE1: [SEQ ID NO:8]

AATCCGGAGGAGACGGTGACCGTGGTCCCTTGGCCCCAG

For the amplification of the V domains via PCR we used the primers 5'L1 and 3'K, flanking the $V_L$, domain, and 5'H1 and 3'G for the heavy chain based on primers described by Dübel et al. (24).

The cDNA of the anti-CD3 scFv fragment was kindly provided by A. Traunecker (25).

Example 2

Construction of Bispecific Single-Chain Fragments and Eukaryotic Expression To obtain an anti-CD19 scFv-fragment, the corresponding $V_L$- and $V_H$-regions cloned into separate plasmid vectors served as templates for a $V_L$- and $V_H$-specific PCR using the oligonucleotide primer pairs 5'$V_L$B5RRV/3'$V_L$GS15 and 5'$V_H$GS15/3'$V_H$BspEI, respectively. Thereby, overlapping complementary sequences were introduced into the PCR-products, that combine to form the coding sequence of 15-amino acid (Gly4Ser1)3-linker (SEQ ID NO:13) during the subsequent fusion-PCR. This amplification step was performed with the primer pair 5'$V_L$B5RRV/3'$V_H$BspEI and the resulting fusion product (or rather anti-CD19 scFv-fragment) was cleaved with the restriction enzymes EcoRV and BspEI and thus cloned into the bluescript KS-vector (Stratagene) containing either the (EcoRI/SalI-cloned) coding sequence of the anti-17-1A/anti-CD3 bispecific single-chain antibody with an N-terminal FLAG-tag [1] or that of the modified version without FLAG/epitope (21), thereby replacing the anti-17-1A- by the anti-CD19-specificity and preserving the 5-amino acid (Gly4Ser1)1-linker (SEQ ID NO:11) connecting the C-terminal anti-CD3 scFv-fragment, respectively. Subsequently, the DNA fragments encoding both versions of the anti-CD19/anti-CD3 bispecific single-chain antibody with the domain arrangement $V_L$CD19-$V_H$CD19-$V_H$CD3-$V_L$CD3 were subcloned EcoRI/SalI into the described expression vector pEF-DHRF [1], respectively. The resulting plasmid DNAs were transfected into DHFR-deficient CHO-cells by electroporation: selection, gene amplification and protein production were preformed as described [1]. In the following examples, results obtained with the FLAG-containing version of bscCD19×CD3 are illustrated.

Figure 1:
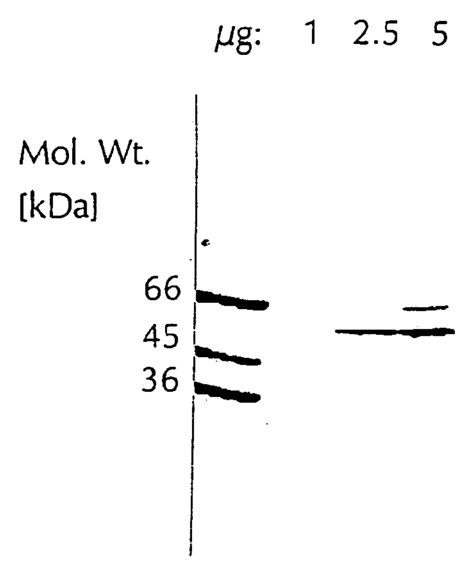
FIG. 1: SDS-Page: Coomassie stain of the purified bscCD19×CD3 fragment with different amounts of protein. Molecular mass (kDa) of the marker is indicated on the left.

Purification of bscCD19×CD3 from the supernatant of transfected CHO cells yielded 4 mg/liter culture supernatant. The bsc-Ab was purified via its C-terminal histidine tail by affinity chromatography on a Ni-NTA-column as described [1]. The bsc-Ab was eluted from the Ni-NTA column as a distinct peak at a concentration of 200 mM imidazole. SDS-Page was carried out according to Laemmli (26) with a 12% gel followed by staining with Coomassie brilliant blue R250 for analyzing the purification of the bsc-Ab. The results of SDS-PAGE analysis (FIG. 1) show the expected size of the bsc-Ab (60 kDa).

Example 3

Binding Properties of the bsc-AbCD19×CD3

Binding specificities of the bsc-Ab to CD3 and CD19 were shown by flow cytometric analysis on CD3-positive Jurkat cells, human PBMCs and a number of different CD19-positive B cell lymphoma cell lines including Blin I, SKW6.4, Daudi, BJAB and Raji. The CD19-positive B cell lines Daudi, Raji, BJAB (Burkitt's lymphoma), SKW6.4 (human EBV transformed B cell) and Blin-1 (pre B cell line) were used in flow cytometric analysis and chromium release assays. Jurkat is a CD3-positive T cell line; BL60 and the plasmacytoma cell lines NCI and L363 are negative for both surface molecules, CD3 and CD19. Cell lines were cultured in complete RPMI 1640 (Biochrom) with 10% FCS (GIBCO).

Figure 2:
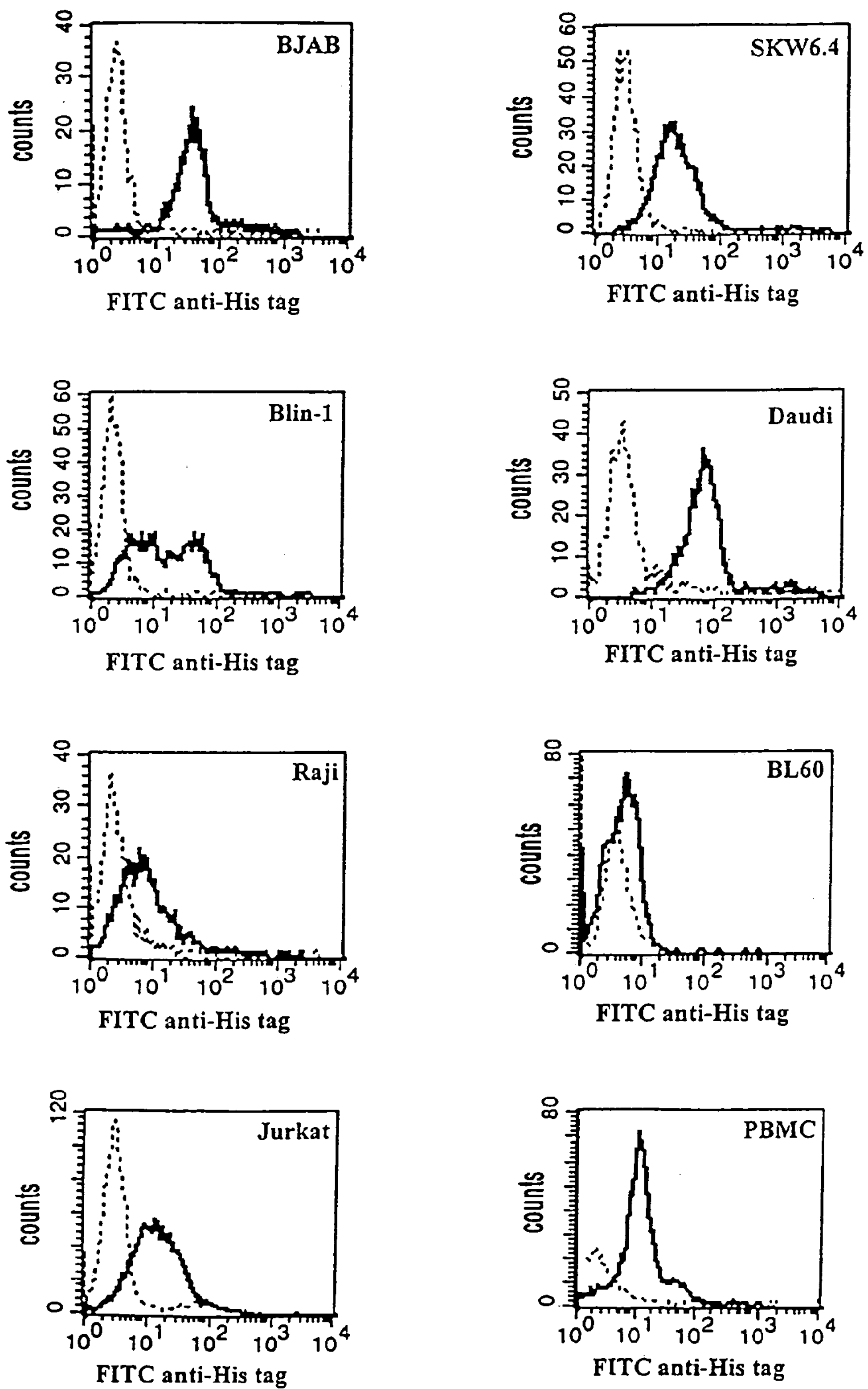
FIG. 2: FACS-analysis with the bscCD19×CD3 (200 μg/ml) on different CD19-positive B cell lines (BJAB, SKW6.4, Blin-1, Daudi, Raji), on the CD19-negative B cell line BL60 and on CD3-positive Jurkat cells and primary human PBMCs. Broken lines indicate negative controls.

$1\times10^6$ cells were washed with PBS, resuspended in 200 µl PBS with 10% Vernimmun (Centeon, Marburg, Germany) and 0.1% NaN3 and incubated for 30 min at 4° C. After a centrifugation step (100×g, 5 min) cells were incubated in 50 µl bscCD19×CD3 (200 µg/ml in PBS with 10% Venimmun and 0.1% $NaN_3$) for 30 min at 4° C. The cells were washed twice with PBS. For the detection of the bsc-Ab a FITC-conjugated antibody against the His-tag (Dianova) was used. The irrelevant bsc-Ab 17-1A×CD3, produced by the same expression system as bscCD19×CD3, or the His-tag antibody alone served as negative controls. Flow Cytometry was performed with a Becton Dickinson FACScan. No binding was detectable on BL60 cells which do express neither CD19 nor CD3 (FIG. 2).

Example 4

Cytotoxic Activity of the bsc-AbCD19×CD3 against CD19-Positive Lymphoma Cells

Figure 3:
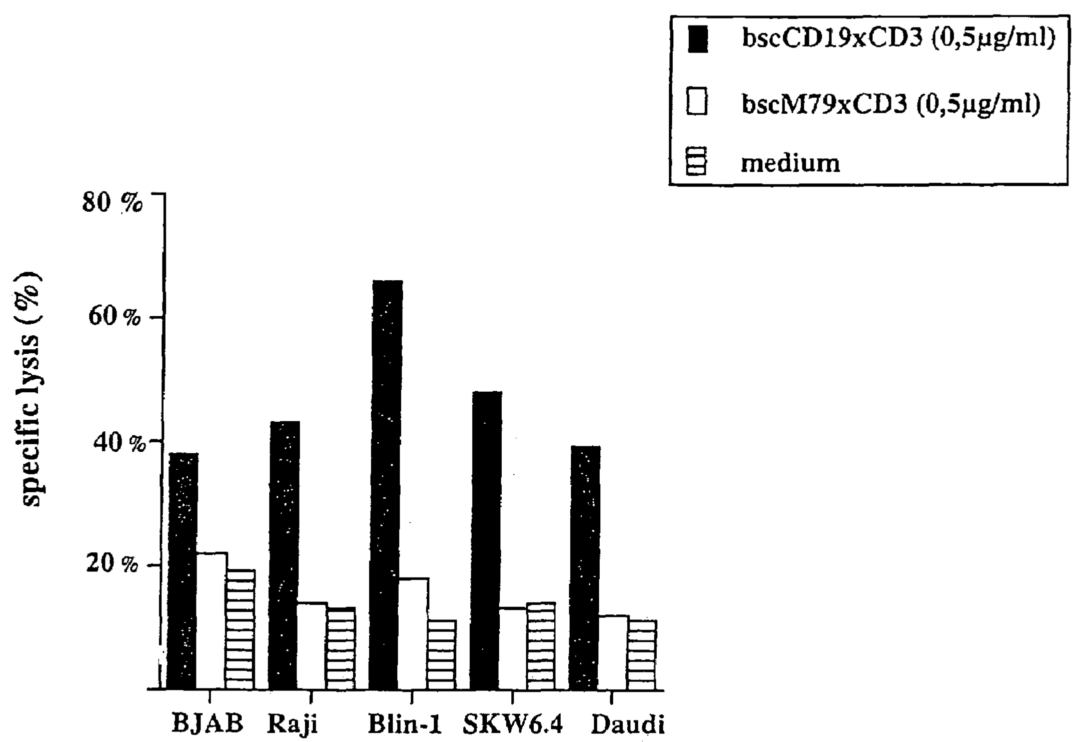
FIG. 3: Cytotoxicity of bscCD19×CD3 in a $^{51}$Cr release assay with unstimulated human PBMCs and different B cell lines. Effector: Target cell ratio 10:1; incubation time 4 h. Standard deviation in all triplicates was below 7%.

The bscCD19×CD3 antibody proved to be highly cytotoxic for several lymphoma cell lines in a $^{51}$Cr release assay (FIG. 3). Human peripheral blood mononuclear cells (PBMCs) as effector cells were isolated from fresh buffy coats of random donors using Lymphoprep™ (Nycomed) gradient centrifugation with subsequent 100×g centrifugation steps to remove thrombocytes. CD19-positive B cells were depleted using Dynabeads® M-450 CD19 (Dynal). The depleted cell populations were analyzed by flow cytometry (Becton Dickinson), which showed a 99% depletion of CD19-positive cells. The PBMCs were incubated over night at 37° C., 5% CO2 CD19-positive B cell lines (Raji, Blin I, Daudi, BJAB, SKW6.4) were used as target cells.

Cytotoxicity was measured in a standard chromium release assay in round-bottom 96-well-plates (Nunc) using RPMI 1640 complete medium (Biochrom) with 10% FCS (GIBCO).

Unstimulated PBMCs were added in a volume of 80 µl medium to each well containing 20 µl of bsc-Ab in different concentrations. Then 100 µl of $^{51}$Cr-labeled target cells ($1\times10^4$) were added, plates were centrifuged for 3 min at 100×g and incubated for 4 h at 37° C., 5% $CO_2$. After an additional centrifugation step 50 µl supernatant was removed and assayed for released $^{51}$Cr in a gamma counter (TopCount, Canberra Packard).

Figure 4:
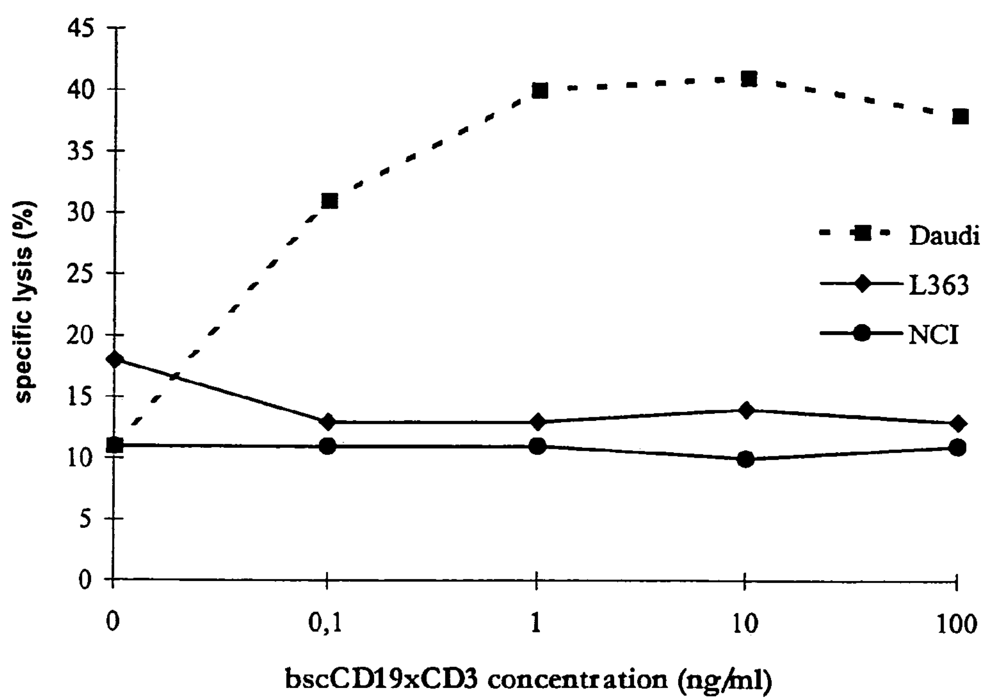
FIG. 4: Chromium release cytotoxicity assay with unstimulated primary human PBLs against the plasmacytoma cell lines L363 and NCI and the lymphoma cell line Daudi E:T ratio 20:1; incubation time 8 h.
Figure 5:
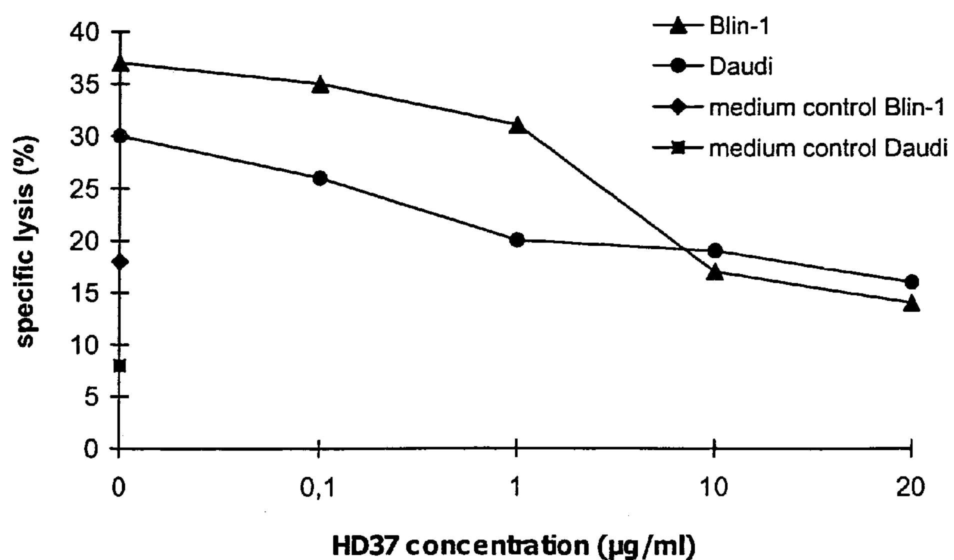
FIG. 5: Inhibition of the cytotoxicity of bscCD19×CD3 by the parental anti-CD19 antibody HD37 in a chromium release assay; incubation time 8 h; E:T ratio 20:1; concentration of bscCD19×CD3 1 ng/ml.
Figure 6:
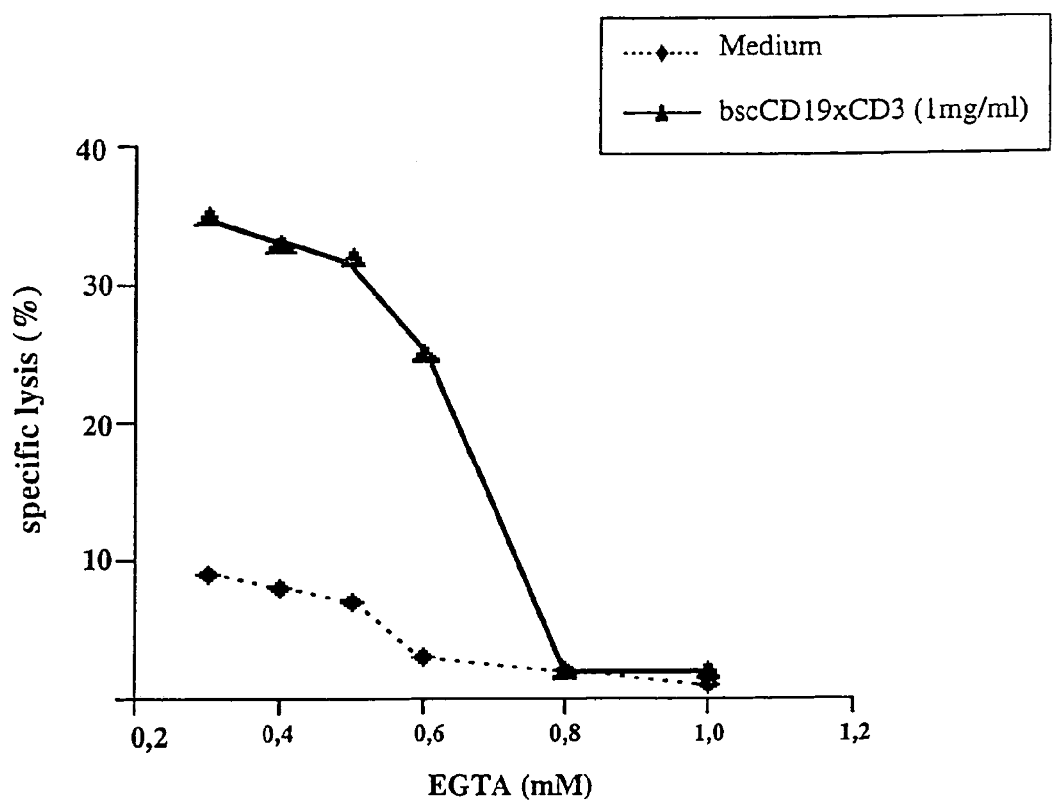
FIG. 6: Cytotoxicity assay with unstimulated PBMCs against Daudi cells after addition of increasing amounts of EGTA, E:T ratio 10:1, incubation time 4 h.

Spontaneous release was measured by incubating the target cells without effector cells or antibodies, and maximal release was determined by incubating the target cells with 10% TritonX-100. Incubation of target cells with bscAb without effector cells did not result in measurable lysis. The percentage specific lysis was calculated aspecific release (%)=[(cpm, experimental release)−(cpm, spontaneous release)]/[(cpm, maximal release)−(cpm, spontaneous release)]×100. All tests were carried out in triplicates. SD within the triplicates was in all experiments below 6%. To approximate the in vivo conditions we used unstimulated PBMCs from healthy donors as effector cells. Rapid induction of cytotoxicity within 4 hours could be observed without any T cell prestimulation protocol. As a control a bsc-antibody with different tumor specificity (bsc 17-1A×CD3) but generated by the same system as the bscCD19×CD3 antibody showed lysis activity not significantly above medium background. In addition, no cytotoxic activity could be observed using the plasmacytoma cell lines NCI and L363 which do not express CD19 as target cells (FIG. 4). In competition assays using increasing amounts of the CD19-specific parental monoclonal antibody HD37 cytotoxic activity of the bscCD19×CD3 could be nearly completely blocked (FIG. 5). These controls show that the bscCD19×CD3-mediated cytotoxic effects are antigen-specific. To get more information about the molecular mechanisms how the bscCD19×CD3 antibody kills CD19-positive target cells we tried to block bscCD19×CD3-mediated cytotoxicity by EGTA. As shown in FIG. 6 cytotoxic activity of bscCD19×CD3 could be completely blocked by EGTA indicating that specific lysis is a T cell-mediated effect (probably via the perforin-pathway) rather than a direct (e.g. apoptosis-inducing) effect of the antibody itself.

Figure 7:
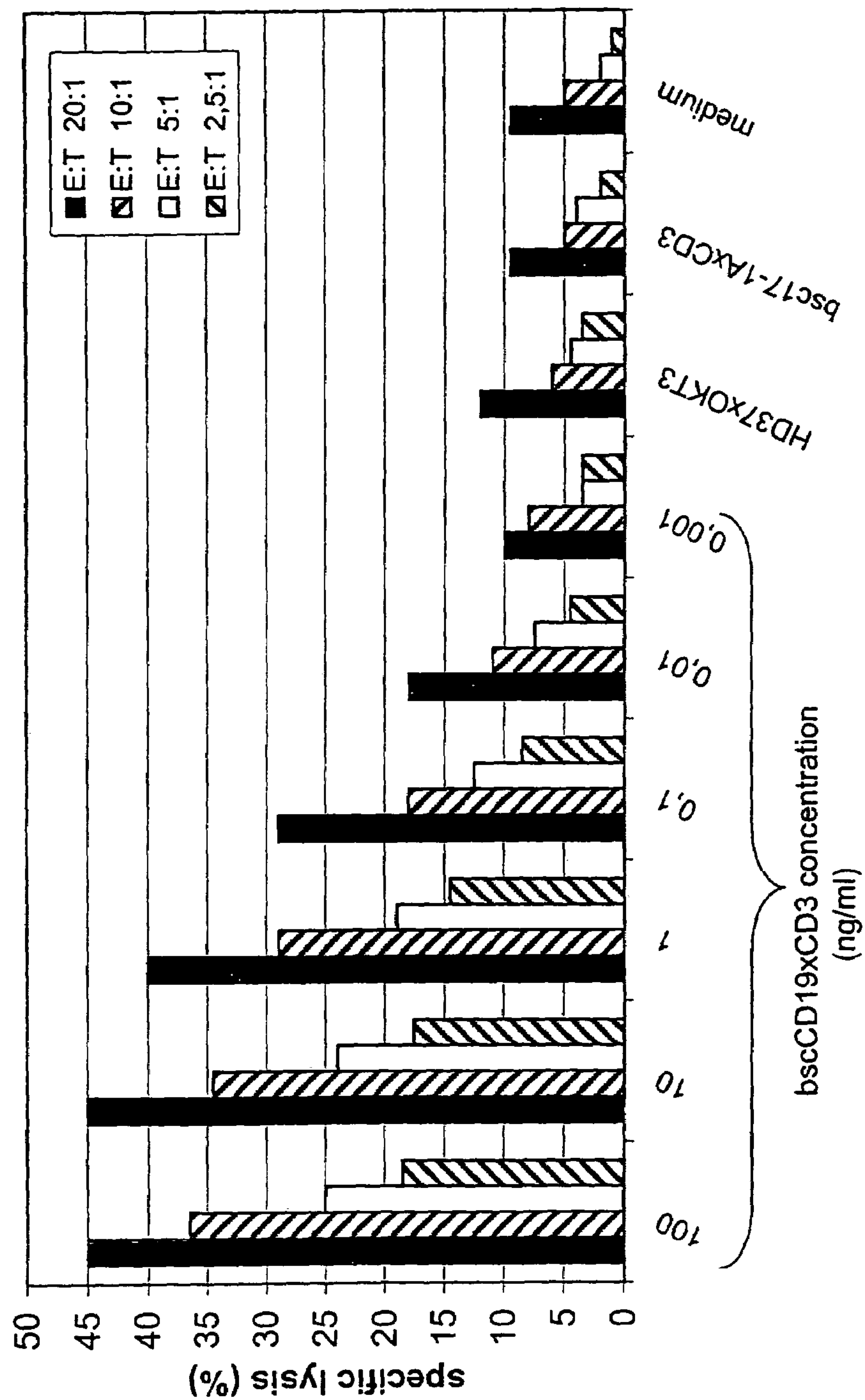
FIG. 7: Cytotoxicity of bscCD19×CD3 in a $^{51}$Cr release assay with unstimulated human PBMCs and Blin-1 as target cells at different E:T ratios; incubation time 4 h; concentration of the conventional bispecific antibody 3 μg/ml; concentration of bsc 17-1A×CD3 100 ng/ml; E:T ratios as indicated.

Using unstimulated T cells even at antibody concentrations below 1 ng/ml a significant cytotoxic effect against Blin-1 cells could be observed (FIG. 7). Even at relatively low E:T ratios (5:1; 2.5:1) and at very low antibody concentrations of 10-100 pg/ml the bscCD19×CD3 antibody could rapidly induce specific cytotoxic activity of unstimulated T cell (FIG. 7). In contrast, a conventional bispecific CD19×CD3 antibody generated by hybrid-hybridoma technique (5-7, 27) did not show significant cytotoxic activity under these conditions even at concentrations up to 3000 ng/ml (FIG. 7). This conventional bispecific antibody required additional T cell prestimulation and high antibody concentrations of about 100 ng/ml to induce specific T cell cytotoxicity (not shown) which is consistent with the literature (5-7, 27).

Example 5

Depletion of Primary (Malignant) B-cells by Autologous T-cells Through the Cytotoxic Activity of bscCD19×CD3

Figure 9:
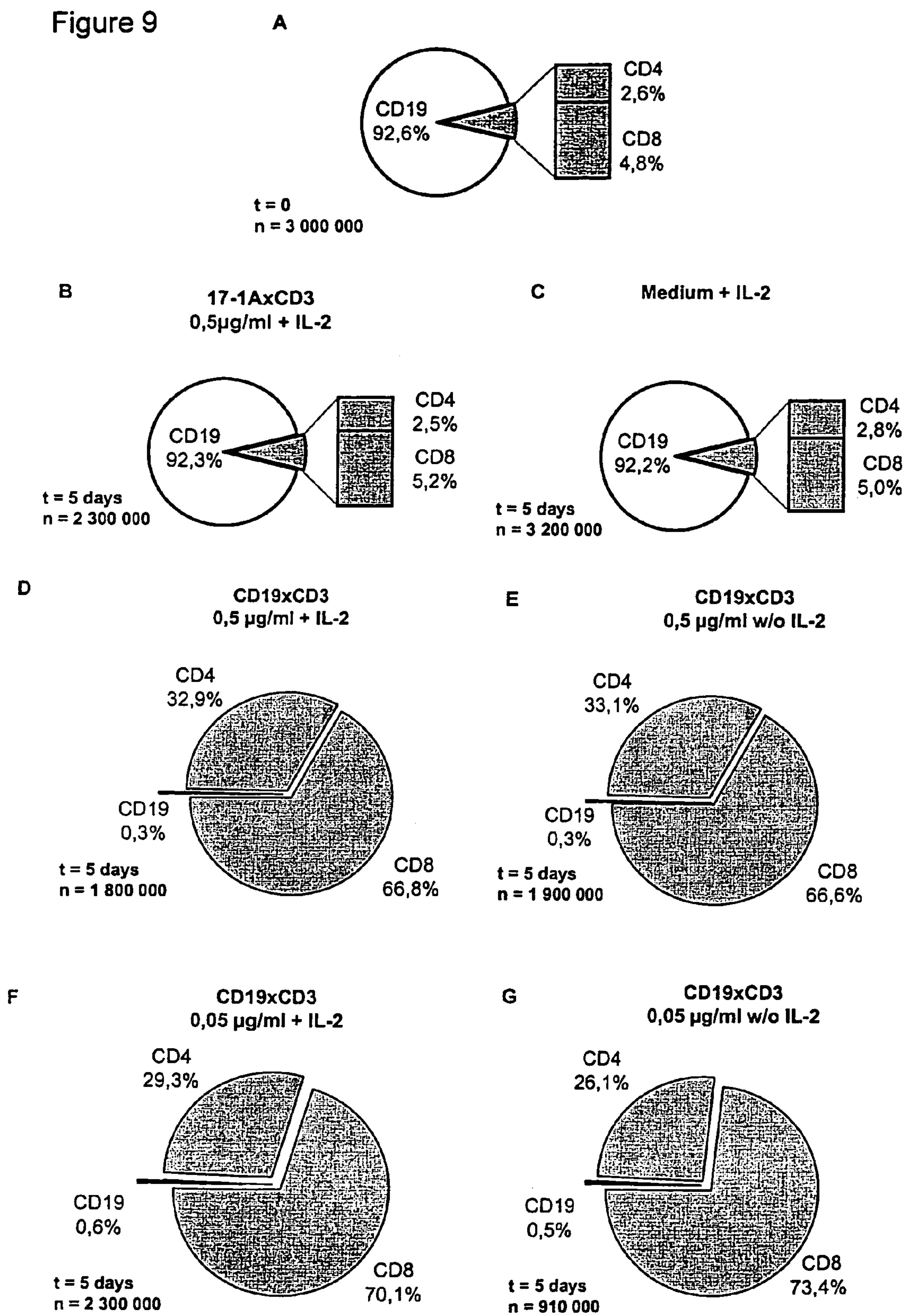
FIG. 9: Depletion of primary (malignant) CD19$^+$ B-cells by recruitment of autologous primary T-lymphocytes through bscCD19×CD3.

In order to assess the cytotoxic activity of bscCD19×CD3 on primary malignant B-cells, mononucleated cells from the peripheral blood (PBMC) of a patient suffering from B-CLL (B-cell derived chronic lymphatic leukemia) were isolated by Ficoll density gradient centrifugation. These cells were consecutively cultured in the presence or absence of bscCD19×CD3 for 5 days at 37° C./5% $CO_2$ in RPMI 1640 medium supplemented with 10% FCS and, optionally, with 60 U/ml IL-2. Flowcytometric analysis revealed that the peripheral blood lymphocytes (PBL) of this particular NHL (Non-Hodgkin lymphoma)-patient (who was later systemically treated with bscCD19×CD3; see example 7) contained 92.6% CD19-positive B-cells (=target cells) and 7.4% CD3-positive T-lymphocytes (=effector cells) at a CD4/CD8 T-cell ratio of 2.6:4.8. The vast majority of these CD19-positive B-cells consisted of malignant cells. $3\times10^6$ PBL/ml per well were seeded in a volume of 1 ml each into a 24-well tissue culture plate. As negative controls served culture medium plus IL-2 and culture medium plus IL-2 with the irrelevant bispecific single chain antibody bsc 17-1A×CD3 (1) at a concentration of 0.5 µg/ml. As shown in FIG. 9, no depletion of CD19-positive cells was detectable under these conditions after 5 days of incubation. However, when bscCD19×CD3 was added at concentrations of 0.5 µg/ml or 0.05 µg/ml (either in the presence or absence of IL-2) almost all CD19-positive B-cells had been killed. The cultured cells at that time consisted mainly of T-lymphocytes with a CD4/CD8 T-cell ratio of approximately 1:2 to 1:3. This demonstrates the exceptional cytotoxicity of bscCD19×CD3 towards CD19-positive B-cells, since total depletion of primary B-cells by autologous T-cells could be induced at a concentration of only 50 ng/ml at a highly unfavorable initial effector target cell ratio of less than 1:10, even without IL-2 or another kind of additional T-cell stimulation.

Example 6

Purification of bscCD19×CD3 for Therapeutic Use

BscCD19×CD3 was produced in Chinese hamster ovary (CHO) cells stably transfected with an expression vector (pEF-DHFR; see example 2) encoding bscCD19×CD3 and, additionally, a hexahistidine and a FLAG tag. Cells were grown in serum-free medium (Rencyte) in a hollow fiber reactor (Unisyn). Five hundred ml of cell culture supernatant were collected and sterile-filtered through a 0.2 μm filter (AcroCap; Pall Gelman).

BscCD19×CD3 was detected and quantitated by western blotting using mouse anti-FLAG IgG (Sigma) and goat-anti-mouse IgG coupled to Alkaline Phosphatase (Sigma). Detection was carried out by chemoluminescence using the BCIP/NBT system (Devitron). Protein concentrations were determined by Bradford assay (Biorad), using bovine IgG (Biorad) as protein standard. Purity of column fractions was assessed by reducing sodium dodecyl sulfate (SDS) Bis/Tris 4-12% polyacrylamide gradient gel electrophoresis (PAGE) employing a MOPS buffer system (Novex).

Purification of bscCD19×CD3 to homogeneity required cation exchange chromatography, cobalt chelate affinity chromatography and, as final step, gel filtration. These purification steps were carried out employing standard protocols (see below). A flow scheme of the purification procedure is shown in FIG. 10.

Cation exchange chromatography: The cell culture supernatant from CHO cells was mixed with two volumes of Buffer C (30 mM morpholinoethane sulfonic acid [MES], 20 mM NaCl, 3 mM EDTA, 0.3 mM benzamidine hydrochloride, pH 5.5) and passed over a 70 ml-SP Sepharose Fast Flow cation exchange column (Pharmacia) at a flow rate of 20 ml/min. The column was equilibrated with Buffer A (20 mM MES, 20 mM NaCl, pH 5.8). After washing with 5 column volumes of Buffer A, bscCD19×CD3 was eluted with a step gradient of 45% Buffer B (20 mM MES, 1 M NaCl, pH 5.8) in Buffer A. The eluate received 0.045 volumes of 1 M Tris/HCl, pH 8.5, containing 47 mM imidazole, and was subsequently sterile-filtered (0.2 μm; AcroCap). A typical elution profile of the cation exchange chromatography is shown in FIG. 12. BscCD19×CD3 was contained in fraction 6.

Cobalt chelate affinity purification: The eluate from the cation exchange column was passed at a flow rate of 2.5 ml/min over a 10 ml-Chelating Sepharose Fast Flow column (Pharmacia) equilibrated in Buffer AO (50 mM Na2HPO4, 400 mM NaCl, pH 8.0). The column had been pre-equilibrated with a solution of 0.1 M cobalt chloride. After washing with 33 column volumes Buffer AO, Buffer A (50 mM Na2HPO4, 400 mM NaCl, 2 mM imidazole, pH 6.4) and a gradient from 0-12% Buffer B (50 mM Na2HPO4, 400 mM NaCl, 500 mM imidazole, pH 6.4) in Buffer A, bscCD19×CD3 was eluted in one step by 30 ml of 100% Buffer B. The eluate was sterile-filtered followed by approximately 10-fold concentration in a MacroSep device (Pall Gelman; 10 kD cut-off). A typical elution profile for the cobalt chelate affinity chromatography is shown in FIG. 13. BscCD19×CD3 was detected in fraction No. 7.

Gel filtration: The concentrated eluate from the cobalt chelate affinity column was loaded at a flow rate of 0.75 ml/min on a 124 ml-High Load Superdex 200 column (Pharmacia; prep grade) equilibrated with phosphate-buffered saline (Gibco). BscCD19×CD3 eluted in a fraction with a molecular size corresponding to approximately 55 kDa (FIG. 14, fraction No. 7). The gel filtration fraction containing bscCD19×CD3 was supplemented with 5% human serum albumin (Behring) followed by sterile-filtration through a 0.1 μm filter (Millex; Millipore).

The abundance of bscCD19×CD3 in the cell culture supernatant and the various active columns fractions, as analyzed by SDS-PAGE, is shown in FIG. 11. BscCD19×CD3 was the major protein band detected in cell culture supernatants (lane 2). Highly purified anti-CD19xanti-CD3, which was used for human therapy, did not show detectable impurities (FIG. 11, lane 5).

Example 7

Clinical Use of bscCD19×CD3 in a Patient with B-cell Lymphoma

In a compassionate use a patient (A-B, female, born 1937) suffering from B-cell derived chronic lymphatic leukemia (B-CLL) has been treated with the bispecific single chain antibody bscCD19×CD3.

Patient History and Rationale:

The patient had been diagnosed with B-CLL in 1992. At the time of initial diagnosis the disease had affected various lymph node regions and the spleen; in addition, hemolytic anemia of autoimmune origin and an immunoglobulin deficiency was observed. The patient has a struma nodosa which is well controlled and in euthyreotic condition by treatment with carbimazol 2.5 mg/d.

The patient had received multiple cycles of chemotherapy with chlorambucil and prednisone from 1992 till 1994. Following progression of the disease, the treatment was changed to cyclophosphamide, doxorubicine, vincristin and prednisone (CHOP, 8 cycles) and a remission was achieved for more than one year. After a new relapse, the patient received another 6 cycles of CHOP, followed by chlorambucil and prednisone and a single course of chlorambucil alone which did not cause any improvement of the disease. In December 1998, irradiation of the spleen was performed to control the progressing splenomegalia of the patient. The patient experienced a profound bone marrow depression with multiple infectious complications. Her anemia and thrombocytopenia required frequent transfusions of red blood cells and platelet substitution.

Due to the advanced stage of the disease and impaired bone marrow function, a more aggressive or high-dose chemotherapy was not indicated in this patient. Treatment with the anti-CD20 antibody rituximab was not appropriate since the efficacy of rituximab in B-CLL was not clearly demonstrated so far.

A FACS analysis revealed that 95% of the patient's peripheral blood cells were CD19 positive cells while 77% of the cells expressed the CD20 antigen. Incubation of the patient's peripheral blood cells with the bscCD19×CD3 showed a pronounced depletion of CD19-positive B-cells (see example 5). Therefore the physicians decided to treat the patient with the novel bscCD19×CD3 in a compassionate use. The patient was informed in detail about the novelty of the compound and about the potential risks and benefits of this treatment. She fully understood the explanations and gave written informed consent for this compassionate use.

Description of the Clinical Administration:

Before starting the treatment, the patient underwent clinical examination and extensive diagnostic procedures to verify the extent of the disease and to exclude any additional risk factors. The patient was in fair clinical condition with anemia, thrombocytopenia and weight loss but without any cardiovascular impairment or other complications preventing the use of the bscCD19×CD3. During the night before the first treatment days the patient suffered from migraine headache. For the administration of the bscCD19×CD3 the patient was kept in the hospital ward under intensive care conditions to ensure rapid treatment of any emergency which might have occurred. To prevent any acute cytokine reactions and complications of tumor lysis, the patient got prophylactic IV doses of 2 mg clemastine (Tavegil®) and 200 mg cimetidine (Tagamet®) as well as 300 mg allopurinol and 20 mg of omeprazol (Antra®).

Alkalization and heparinization were performed throughout the treatment and the follow-up periods. In addition, the patient received all necessary symptomatic treatment.

Blood samples were taken before and during the administration of the drug to follow biochemical, hematological and immunological parameters.

1st Administration of bscCD19×CD3 (Apr. 14, 1999):

The patient received a first dose of 3 μg bscCD19×CD3 as 20 min-infusion in isotonic phosphate buffer containing 5% human serum albumin (HSA). During the infusion the patient did not have any adverse effects. About 1 hour after infusion the patient had chills for about 5 minutes followed by sweating, a moderate decrease of blood pressure by about 10 mmHg and a moderate increase of body temperature (+0.5° C.) for a few hours. In addition, her headache slightly worsened. The patient was treated with another 2 mg of Tavegil® and 200 mg of Tagamet®, 250 mg prednisolone (Solu-Decortin®) and 50 mg pethidine (Dolantin®). All symptoms released without sequelae the same day.

2nd Administration of bscCD19×CD3 (Apr. 15, 1999):

A second dose of 10 μg bscCD19×CD3 was given one day later under the same conditions. About 1 hour after infusion the patients had remarkable chills, fever (39.2° C.), slight hyperventilation and a hypotensive reaction. The patient was treated with 2 mg Tavegil, 200 mg Tagamet and 300 mg Solu-Decortin and 15 mg piritramide (Dipidolor®). For stabilization of her cardiovascular function the patient received a dopamine infusion and got volume substitution. Following this treatment the symptoms decreased remarkably. Nevertheless, the patient was transferred to the cardiology department overnight to ensure proper monitoring of vital signs and immediate intervention in case of emergency. The patient was transferred to the normal ward the next morning without having any further complications.

During the next 3 days the patient continued having subfebrile temperature (about 37.2° C.) and developed minor pleural effusion one day later the second dose (Apr. 16, 1999) and mild edema of the lower extremities (Apr. 18, 1999). Cardiovascular function remained stable and the laboratory evaluations revealed no remarkable changes with respect to safety, except for an increase of γ-glutamyltransferase after the second dose of bscCD19×CD3 (FIG. 15).

Since bscCD19×CD3 was tolerated by the patient and the adverse effects could be controlled with symptomatic treatment, the administration of the novel bscCD19×CD3 will be continued in this patient.

Clinical and Immunological Efficacy of bscCD19×CD3:

Clinical Results:

Ultrasound examination of the spleen and five abdominal and axillary lymph nodes was performed one day and 4 days after administration of the second dose of bscCD19×CD3. Already one day after the 10 μg dose (Apr. 16, 1999), the lymph nodes as well as the spleen showed a shrinkage of about 20% as compared to the baseline evaluation. This observation was confirmed in a second ultrasound evaluation on Apr. 19, 1999. The weight of the spleen decreased by 350 g (from 1630 g at baseline to 1280 g on Apr. 19, 1999) (table 1; FIG. 16).

Hematological Results:

The number of white blood cells, which include mostly malignant B-cells, decreased during the course of the treatment and the follow-up days (table 2; FIG. 17). The C-reactive protein (CRP) is an acute phase reaction protein which reflects T-cell activation and the effect of pro-inflammatory cytokines. It increased remarkably after administration of 10 μg bscCD19×CD3, followed by a continuous decrease during the next 3 observation days (table 2; FIG. 18).

Immunological Results:

The level of serum cytokines which reflects the acute immunological response to the administration of the compound, was measured before and at various intervals after administration of the novel compound. Serum levels of cytokines and of the soluble IL-2 receptor were measured by a quantitative ELISA assay according to the instructions of the manufacturer.

Tumor necrosis factor TNF-α increased significantly in a dose-dependent manner within the first hour after administration of bscCD19×CD3 (FIG. 19).

Interleukin 6 (IL-6) and interleukin 8 (IL-8) also showed a significant and dose dependent increase. Their maximum levels were observed 2 to 4 hours after administration of the bscCD19×CD3 (FIGS. 20, 21). All cytokines returned to baseline levels within a few hours.

The soluble IL-2 receptor was elevated already at baseline which may be explained by the mass of malignant B-cells expressing the IL-2 receptor. Following administration of the novel bscCD19×CD3, an increase of the soluble IL-2 receptor was observed, which indicates an activation of effector cells (FIG. 22).

CONCLUSION

The novel bscCD19-CD3 was administered safely to a patient suffering from refractory B-CLL. The tolerability of the bscCD19×CD3 at the doses of 3 μg and 10 μg was acceptable and could be controlled well by means of prophylactic measures and symptomatic treatment.

The novel bscCD19×CD3 caused a shrinkage of the previously enlarged spleen and lymph nodes of the patient, as shown in the ultrasound examination. Since enlargement of spleen and lymph nodes is caused by infiltrations with malignant B-cells, the shrinkage reflects the destruction of malignant B-cells as result of administration of bscCD19×CD3.

In sharp contrast to any other bispecific CD19×CD3 antibody known in the art, the bispecific CD19×CD3 antibody of the invention (bscCD19×CD3) exhibits clinical efficacy in B-cell derived non-Hodgkin lymphoma as measured by the shrinkage of lymphoid organs infiltrated by malignant B-cells. Advantageously, bscCD19×CD3 proved to be clinically effective at surprisingly low doses which are well-tolerated after systemic administration. Thus, the clinical efficacy of bscCD19×CD3 confirms its exceptional cytotoxic activity as determined in vitro.

REFERENCES

1. Mack, Proc. Natl. Acad. Sci. USA 92 (1995), 7021-5
2. Gianni, N Engl. J. Med. 336 (1997), 1290-7
3. Urba, J. Natl. Cancer Inst. Monogr. (1990), 29-37
4. Fisher, Cancer (1994)
5. Bohlen, Blood 82 (1993), 1803-121
6. Bohlen, Cancer Res 53 (1993), 18:4310-4.
7. Bohlen, Cancer Res 57 (1997), 1704-9.
8. Haagen, Clin Exp Immunol 90 (1992), 368-75.
9. Haagen, Cancer Immunol Immunother. 39 (1994), 391-6.
10. Haagen, Blood 84 (1994), 556-63.
11. Haagen, Blood 85 (1995), 3208-12.
12. Weiner, Leuk Lymphoma 16 (1995), 199-207.
13. Csoka, Leukemia 10 (1996), 1765-72.
14. Uckun, Proc. Natl. Acad. Sci. USA 85 (1988), 8603-7.
15. Staerz, Proc. Natl. Acad. Sci. USA 83 (1986), 1453-7.
16. Lanzavecchia, Eur J Immunol 17 (1987), 105-11.
17. Mallender, J Biol Chem 269 (1994), 199-206.
18. Gruber, J Immunol 152 (1994), 5368-74.
19. Kostelny, J Immunol 148 (1992), 1547-53.
20. Mack, J Immunol 158 (1997), 3965-70.
21. Kufer, Cancer Immunol Immunother 45 (1997), 193-7.
22. Pezzutto, J Immunol 138 (1987), 2793-9.
23. Orlandi, Proc. Natl. Acad. Sci. USA 86 (1989), 3833-7.
24. Dubel, J Immunol Methods 175 (1994), 89-95.
25. Traunecker, Embo J 10 (1991), 3655-9.
26. Laemmli, Nature 227 (1970), 680-5.
27. Bohlen, J Immunol Methods 173 (1994), 55-62.
28. Demanet, Int J Cancer Suppl 7 (1992), 67-8.
29. De, J Hematother 4 (1995), 433-7.
30. Haagen, Leuk Lymphoma 19 (1995), 381-93.
31. Anderson, Blood 80 (1992), 2826-34.
32. Zhu, Int J Cancer 62 (1995), 319-24.
33. Hartmann, Blood 89(1997), 2042-7.
34. Valone, J Clin Oncol 13 (1995), 2281-92.
35. Valone, J Hematother 4 (1995), 471-5.
36. Bolhuis, Int J Cancer Suppl 7 (1992), 78-81.
37. Canevari, J Natl Cancer Inst 87 (1995), 1463-9.
38. Nitta, Lancet 335 (1990), 368-71.
39. Yokota, Cancer Res 52 (1992), 3402-8.
40. Weiner, J Immunol 152 (1994), 2385-92.
41. Maloney, Blood 84 (1994), 2457-66.
42. Reff, Blood 83 (1994), 435-45.
43. Kipriyanov, Int. J. Cancer 77 (1998), 763-772.

TABLE 1

The effect of bscCD19xCD3 on the size of lymph nodes and spleen in a patient suffering from B-cell lymphoma.

| Ultrasound measurements | | | April, 12$^{th}$ 1999 | April, 16$^{th}$ 1999 | April, 19$^{th}$ 1999 |
|---|---|---|---|---|---|
| Lymph nodes | abdominal | 1) | 54 × 29 × 14 mm | 42 × 30 × 13 mm | 42 × 30 × 14 mm |
| | | 2) | 56 × 33 × 18 mm | 43 × 33 × 18 mm | 43 × 30 × 16 mm |
| | | 3) | 46 × 32 × 27 mm | 46 × 31 × 22 mm | 47 × 32 × 23 mm |
| | axillary | left | 36 × 24 × 16 mm | 34 × 22 × 15 mm | 30 × 22 × 14 mm |
| | | right | 37 × 24 × 13 mm | 33 × 20 × 11 mm | 32 × 23 × 14 mm |
| spleen | | | 270 × 146 × 69 mm | 265 × 132 × 64 mm | 265 × 128 × 63 mm |
| | | | 1630 g | 1340 g | 1280 g |

The sizes of three abdominal lymph nodes, one left and one right axillary lymph node and of the spleen were determined and measured by sonography using a Toshiba SSA100 device. Sizes are given in three dimensions and in mm. The weight of the spleen was calculated from its dimension and ultra sound density.

TABLE 2

Blood levels of selected markers in response to treatments with bscCD19xCD3.

| | Units | Apr. 14, 1999 | Apr. 15, 1999 | Apr. 16, 1999 | Apr. 17, 1999 | Apr. 18, 1999 | Apr. 19, 1999 |
|---|---|---|---|---|---|---|---|
| GGT | U/l | 22 | 24 (morning) | 124 (6.00 h) | 96 | 89 | 87 |
| | | | — (evening) | 107 (12.00 h) | | | |
| LDH | U/l | 618 | 536 (morning) | 548 | 697 | 551 | 539 |
| | | | 773 (evening) | | | | |
| Leukocytes | Gpt/l | 46.8 | 43.3 (morning) | 36.9 | 37.0 | 28.3 | 36.6 |
| | | | 22.3 (evening) | | | | |
| Lymphocytes | % | 85 | 58.8 (morning) | 60.9 | 64.4 | 65.5 | 88 |
| | | | 82.0 (evening) | | | | |
| CRP | mg/dl | <0.4 | 1.0 (morning) | 5.2 | 2.5 | 2.0 | 0.7 |
| | | | 0.7 (evening) | | | | |

Blood levels of gamma-glutamyl transferase (GGT), lactate dehydrogenase (LDH) and C-reactive protein (CRP) were determined by standard clinical biochemistry methods and are expressed as Units/ml (GGT), Units/l (LDH) and mg/dl (CRP). The number of leukocytes is expressed as Giga points/l, and lymphocyte numbers are presented as percent of total leukocytes. Baseline levels on Apr. 14, 1999, before treatment are given in the first lane. The response to 3 μg bscCD19×CD3 on April 15$^{th}$ (which was administered on April 14$^{th}$) is shown in the second lane. The response to a second treatment with 10 μg compound on the same day is shown in the third lane. Blood levels of the selected markers on four days following the drug treatments are given in the last four columns.

What is claimed is:

1. A polynucleotide which upon expression encodes a single-chain multi-functional polypeptide comprising (a) a first domain comprising a binding-site of an antibody or an immunoglobulin chain thereof specifically recognizing the CD 19 antigen; and (b) a second domain comprising a binding site of an antibody or an immunoglobulin chain thereof recognizing the human CD3 antigen;

wherein said domains are arranged in the order $V_L$CD19-$V_H$-CD19-$V_H$CD3-$V_L$CD3.

2. A vector comprising the polynucleotide of claim 1.

3. An isolated host cell transfected with the polynucleotide of claim 1.

4. A An isolated host cell transfected with the vector of claim 2.

* * * * *

UNITED STATES PATENT AND TRADEMARK OFFICE

CERTIFICATE OF CORRECTION

PATENT NO. : 7,575,923 B2
APPLICATION NO. : 11/418058
DATED : August 18, 2009
INVENTOR(S) : Dorken et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 107 days.

Signed and Sealed this

Seventh Day of September, 2010

David J. Kappos

*Director of the United States Patent and Trademark Office*

SEQUENCE LISTING

```
<160> NUMBER OF SEQ ID NOS: 13

<210> SEQ ID NO 1
<211> LENGTH: 36
<212> TYPE: DNA
<213> ORGANISM: Artificial Sequence
<220> FEATURE:
<223> OTHER INFORMATION: Primer

<400> SEQUENCE: 1

gaagcacgcg tagatatckt gmtsacccaa wctcca                                36


<210> SEQ ID NO 2
<211> LENGTH: 30
<212> TYPE: DNA
<213> ORGANISM: Artificial Sequence
<220> FEATURE:
<223> OTHER INFORMATION: Primer

<400> SEQUENCE: 2

gaagatggat ccagcggccg cagcatcagc                                       30


<210> SEQ ID NO 3
<211> LENGTH: 33
<212> TYPE: DNA
<213> ORGANISM: Artificial Sequence
<220> FEATURE:
<223> OTHER INFORMATION: Primer

<400> SEQUENCE: 3

cagccggcca tggcgcaggt scagctgcag sag                                   33


<210> SEQ ID NO 4
<211> LENGTH: 39
<212> TYPE: DNA
<213> ORGANISM: Artificial Sequence
<220> FEATURE:
<223> OTHER INFORMATION: Primer

<400> SEQUENCE: 4

accaggggcc agtggataga caagcttggg tgtcgtttt                             39


<210> SEQ ID NO 5
<211> LENGTH: 36
<212> TYPE: DNA
<213> ORGANISM: Artificial Sequence
<220> FEATURE:
<223> OTHER INFORMATION: Primer

<400> SEQUENCE: 5

aggtgtacac tccatatcca gctgacccag tctcca                                36


<210> SEQ ID NO 6
<211> LENGTH: 48
<212> TYPE: DNA
<213> ORGANISM: Artificial Sequence
```

-continued

```
<220> FEATURE:
<223> OTHER INFORMATION: Primer

<400> SEQUENCE: 6

ggagccgccg ccgccagaac caccaccttt gatctcgagc ttggtccc                48


<210> SEQ ID NO 7
<211> LENGTH: 48
<212> TYPE: DNA
<213> ORGANISM: Artificial Sequence
<220> FEATURE:
<223> OTHER INFORMATION: Primer

<400> SEQUENCE: 7

ggcggcggcg gctccggtgg tggtggttct caggtactgc agagtcgg                48


<210> SEQ ID NO 8
<211> LENGTH: 39
<212> TYPE: DNA
<213> ORGANISM: Artificial Sequence
<220> FEATURE:
<223> OTHER INFORMATION: Primer

<400> SEQUENCE: 8

aatccggagg agacggtgac cgtggtccct tggccccag                          39


<210> SEQ ID NO 9
<211> LENGTH: 1611
<212> TYPE: DNA
<213> ORGANISM: Homo sapiens
<220> FEATURE:
<221> NAME/KEY: CDS
<222> LOCATION: (11)..(1603)
<223> OTHER INFORMATION:

<400> SEQUENCE: 9

gaattccacc atg gga tgg agc tgt atc atc ctc ttc ttg gta gca aca      49
           Met Gly Trp Ser Cys Ile Ile Leu Phe Leu Val Ala Thr
           1               5                   10

gct aca ggt gtc cac tcc gac tac aaa gat gat gac gat aag gat atc     97
Ala Thr Gly Val His Ser Asp Tyr Lys Asp Asp Asp Asp Lys Asp Ile
    15                  20                  25

cag ctg acc cag tct cca gct tct ttg gct gtg tct cta ggg cag agg    145
Gln Leu Thr Gln Ser Pro Ala Ser Leu Ala Val Ser Leu Gly Gln Arg
30                  35                  40                  45

gcc acc atc tcc tgc aag gcc agc caa agt gtt gat tat gat ggt gat    193
Ala Thr Ile Ser Cys Lys Ala Ser Gln Ser Val Asp Tyr Asp Gly Asp
                50                  55                  60

agt tat ttg aac tgg tac caa cag att cca gga cag cca ccc aaa ctc    241
Ser Tyr Leu Asn Trp Tyr Gln Gln Ile Pro Gly Gln Pro Pro Lys Leu
            65                  70                  75

ctc atc tat gat gca tcc aat cta gtt tct ggg atc cca ccc agg ttt    289
Leu Ile Tyr Asp Ala Ser Asn Leu Val Ser Gly Ile Pro Pro Arg Phe
        80                  85                  90

agt ggc agt ggg tct ggg aca gac ttc acc ctc aac atc cat cct gtg    337
Ser Gly Ser Gly Ser Gly Thr Asp Phe Thr Leu Asn Ile His Pro Val
    95                  100                 105

gag aag gtg gat gct gca acc tat cac tgt cag caa agt act gag gat    385
Glu Lys Val Asp Ala Ala Thr Tyr His Cys Gln Gln Ser Thr Glu Asp
110                 115                 120                 125

ccg tgg acg ttc ggt gga ggg acc aag ctc gag atc aaa ggt ggt ggt    433
Pro Trp Thr Phe Gly Gly Gly Thr Lys Leu Glu Ile Lys Gly Gly Gly
                130                 135                 140
```

-continued

```
ggt tct ggc ggc ggc ggc tcc ggt ggt ggt ggt tct cag gtg cag ctg      481
Gly Ser Gly Gly Gly Gly Ser Gly Gly Gly Gly Ser Gln Val Gln Leu
            145                 150                 155

cag cag tct ggg gct gag ctg gtg agg cct ggg tcc tca gtg aag att      529
Gln Gln Ser Gly Ala Glu Leu Val Arg Pro Gly Ser Ser Val Lys Ile
        160                 165                 170

tcc tgc aag gct tct ggc tat gca ttc agt agc tac tgg atg aac tgg      577
Ser Cys Lys Ala Ser Gly Tyr Ala Phe Ser Ser Tyr Trp Met Asn Trp
    175                 180                 185

gtg aag cag agg cct gga cag ggt ctt gag tgg att gga cag att tgg      625
Val Lys Gln Arg Pro Gly Gln Gly Leu Glu Trp Ile Gly Gln Ile Trp
190                 195                 200                 205

cct gga gat ggt gat act aac tac aat gga aag ttc aag ggt aaa gcc      673
Pro Gly Asp Gly Asp Thr Asn Tyr Asn Gly Lys Phe Lys Gly Lys Ala
                210                 215                 220

act ctg act gca gac gaa tcc tcc agc aca gcc tac atg caa ctc agc      721
Thr Leu Thr Ala Asp Glu Ser Ser Ser Thr Ala Tyr Met Gln Leu Ser
            225                 230                 235

agc cta gca tct gag gac tct gcg gtc tat ttc tgt gca aga cgg gag      769
Ser Leu Ala Ser Glu Asp Ser Ala Val Tyr Phe Cys Ala Arg Arg Glu
        240                 245                 250

act acg acg gta ggc cgt tat tac tat gct atg gac tac tgg ggc caa      817
Thr Thr Thr Val Gly Arg Tyr Tyr Tyr Ala Met Asp Tyr Trp Gly Gln
    255                 260                 265

ggg acc acg gtc acc gtc tcc tcc gga ggt ggt gga tcc gat atc aaa      865
Gly Thr Thr Val Thr Val Ser Ser Gly Gly Gly Gly Ser Asp Ile Lys
270                 275                 280                 285

ctg cag cag tca ggg gct gaa ctg gca aga cct ggg gcc tca gtg aag      913
Leu Gln Gln Ser Gly Ala Glu Leu Ala Arg Pro Gly Ala Ser Val Lys
                290                 295                 300

atg tcc tgc aag act tct ggc tac acc ttt act agg tac acg atg cac      961
Met Ser Cys Lys Thr Ser Gly Tyr Thr Phe Thr Arg Tyr Thr Met His
            305                 310                 315

tgg gta aaa cag agg cct gga cag ggt ctg gaa tgg att gga tac att     1009
Trp Val Lys Gln Arg Pro Gly Gln Gly Leu Glu Trp Ile Gly Tyr Ile
        320                 325                 330

aat cct agc cgt ggt tat act aat tac aat cag aag ttc aag gac aag     1057
Asn Pro Ser Arg Gly Tyr Thr Asn Tyr Asn Gln Lys Phe Lys Asp Lys
    335                 340                 345

gcc aca ttg act aca gac aaa tcc tcc agc aca gcc tac atg caa ctg     1105
Ala Thr Leu Thr Thr Asp Lys Ser Ser Ser Thr Ala Tyr Met Gln Leu
350                 355                 360                 365

agc agc ctg aca tct gag gac tct gca gtc tat tac tgt gca aga tat     1153
Ser Ser Leu Thr Ser Glu Asp Ser Ala Val Tyr Tyr Cys Ala Arg Tyr
                370                 375                 380

tat gat gat cat tac tgc ctt gac tac tgg ggc caa ggc acc act ctc     1201
Tyr Asp Asp His Tyr Cys Leu Asp Tyr Trp Gly Gln Gly Thr Thr Leu
            385                 390                 395

aca gtc tcc tca gtc gaa ggt gga agt gga ggt tct ggt gga agt gga     1249
Thr Val Ser Ser Val Glu Gly Gly Ser Gly Gly Ser Gly Gly Ser Gly
        400                 405                 410

ggt tca ggt gga gtc gac gac att cag ctg acc cag tct cca gca atc     1297
Gly Ser Gly Gly Val Asp Asp Ile Gln Leu Thr Gln Ser Pro Ala Ile
    415                 420                 425

atg tct gca tct cca ggg gag aag gtc acc atg acc tgc aga gcc agt     1345
Met Ser Ala Ser Pro Gly Glu Lys Val Thr Met Thr Cys Arg Ala Ser
430                 435                 440                 445

tca agt gta agt tac atg aac tgg tac cag cag aag tca ggc acc tcc     1393
Ser Ser Val Ser Tyr Met Asn Trp Tyr Gln Gln Lys Ser Gly Thr Ser
                450                 455                 460
```

```
ccc aaa aga tgg att tat gac aca tcc aaa gtg gct tct gga gtc cct      1441
Pro Lys Arg Trp Ile Tyr Asp Thr Ser Lys Val Ala Ser Gly Val Pro
            465                 470                 475

tat cgc ttc agt ggc agt ggg tct ggg acc tca tac tct ctc aca atc      1489
Tyr Arg Phe Ser Gly Ser Gly Ser Gly Thr Ser Tyr Ser Leu Thr Ile
        480                 485                 490

agc agc atg gag gct gaa gat gct gcc act tat tac tgc caa cag tgg      1537
Ser Ser Met Glu Ala Glu Asp Ala Ala Thr Tyr Tyr Cys Gln Gln Trp
    495                 500                 505

agt agt aac ccg ctc acg ttc ggt gct ggg acc aag ctg gag ctg aaa      1585
Ser Ser Asn Pro Leu Thr Phe Gly Ala Gly Thr Lys Leu Glu Leu Lys
510                 515                 520                 525

cat cat cac cat cat cat tagtcgac                                     1611
His His His His His His
                530


<210> SEQ ID NO 10
<211> LENGTH: 531
<212> TYPE: PRT
<213> ORGANISM: Homo sapiens

<400> SEQUENCE: 10

Met Gly Trp Ser Cys Ile Ile Leu Phe Leu Val Ala Thr Ala Thr Gly
1               5                   10                  15

Val His Ser Asp Tyr Lys Asp Asp Asp Asp Lys Asp Ile Gln Leu Thr
            20                  25                  30

Gln Ser Pro Ala Ser Leu Ala Val Ser Leu Gly Gln Arg Ala Thr Ile
        35                  40                  45

Ser Cys Lys Ala Ser Gln Ser Val Asp Tyr Asp Gly Asp Ser Tyr Leu
    50                  55                  60

Asn Trp Tyr Gln Gln Ile Pro Gly Gln Pro Pro Lys Leu Leu Ile Tyr
65                  70                  75                  80

Asp Ala Ser Asn Leu Val Ser Gly Ile Pro Pro Arg Phe Ser Gly Ser
                85                  90                  95

Gly Ser Gly Thr Asp Phe Thr Leu Asn Ile His Pro Val Glu Lys Val
            100                 105                 110

Asp Ala Ala Thr Tyr His Cys Gln Gln Ser Thr Glu Asp Pro Trp Thr
        115                 120                 125

Phe Gly Gly Gly Thr Lys Leu Glu Ile Lys Gly Gly Gly Gly Ser Gly
    130                 135                 140

Gly Gly Gly Ser Gly Gly Gly Gly Ser Gln Val Gln Leu Gln Gln Ser
145                 150                 155                 160

Gly Ala Glu Leu Val Arg Pro Gly Ser Ser Val Lys Ile Ser Cys Lys
                165                 170                 175

Ala Ser Gly Tyr Ala Phe Ser Ser Tyr Trp Met Asn Trp Val Lys Gln
            180                 185                 190

Arg Pro Gly Gln Gly Leu Glu Trp Ile Gly Gln Ile Trp Pro Gly Asp
        195                 200                 205

Gly Asp Thr Asn Tyr Asn Gly Lys Phe Lys Gly Lys Ala Thr Leu Thr
    210                 215                 220

Ala Asp Glu Ser Ser Ser Thr Ala Tyr Met Gln Leu Ser Ser Leu Ala
225                 230                 235                 240

Ser Glu Asp Ser Ala Val Tyr Phe Cys Ala Arg Arg Glu Thr Thr Thr
                245                 250                 255

Val Gly Arg Tyr Tyr Tyr Ala Met Asp Tyr Trp Gly Gln Gly Thr Thr
            260                 265                 270
```

-continued

```
Val Thr Val Ser Ser Gly Gly Gly Gly Ser Asp Ile Lys Leu Gln Gln
        275                 280                 285

Ser Gly Ala Glu Leu Ala Arg Pro Gly Ala Ser Val Lys Met Ser Cys
    290                 295                 300

Lys Thr Ser Gly Tyr Thr Phe Thr Arg Tyr Thr Met His Trp Val Lys
305                 310                 315                 320

Gln Arg Pro Gly Gln Gly Leu Glu Trp Ile Gly Tyr Ile Asn Pro Ser
                325                 330                 335

Arg Gly Tyr Thr Asn Tyr Asn Gln Lys Phe Lys Asp Lys Ala Thr Leu
            340                 345                 350

Thr Thr Asp Lys Ser Ser Ser Thr Ala Tyr Met Gln Leu Ser Ser Leu
        355                 360                 365

Thr Ser Glu Asp Ser Ala Val Tyr Tyr Cys Ala Arg Tyr Tyr Asp Asp
    370                 375                 380

His Tyr Cys Leu Asp Tyr Trp Gly Gln Gly Thr Thr Leu Thr Val Ser
385                 390                 395                 400

Ser Val Glu Gly Gly Ser Gly Gly Ser Gly Gly Ser Gly Gly Ser Gly
                405                 410                 415

Gly Val Asp Asp Ile Gln Leu Thr Gln Ser Pro Ala Ile Met Ser Ala
            420                 425                 430

Ser Pro Gly Glu Lys Val Thr Met Thr Cys Arg Ala Ser Ser Ser Val
        435                 440                 445

Ser Tyr Met Asn Trp Tyr Gln Gln Lys Ser Gly Thr Ser Pro Lys Arg
    450                 455                 460

Trp Ile Tyr Asp Thr Ser Lys Val Ala Ser Gly Val Pro Tyr Arg Phe
465                 470                 475                 480

Ser Gly Ser Gly Ser Gly Thr Ser Tyr Ser Leu Thr Ile Ser Ser Met
                485                 490                 495

Glu Ala Glu Asp Ala Ala Thr Tyr Tyr Cys Gln Gln Trp Ser Ser Asn
            500                 505                 510

Pro Leu Thr Phe Gly Ala Gly Thr Lys Leu Glu Leu Lys His His His
        515                 520                 525

His His His
    530


<210> SEQ ID NO 11
<211> LENGTH: 5
<212> TYPE: PRT
<213> ORGANISM: Artificial Sequence
<220> FEATURE:
<223> OTHER INFORMATION: Polypeptide Linker

<400> SEQUENCE: 11

Gly Gly Gly Gly Ser
1               5


<210> SEQ ID NO 12
<211> LENGTH: 4
<212> TYPE: PRT
<213> ORGANISM: Homo sapiens

<400> SEQUENCE: 12

Asp Tyr Lys Asp
1


<210> SEQ ID NO 13
<211> LENGTH: 15
```

-continued

```
<212> TYPE: PRT
<213> ORGANISM: Artificial Sequence
<220> FEATURE:
<223> OTHER INFORMATION: Polypeptide Linker

<400> SEQUENCE: 13

Gly Gly Gly Gly Ser Gly Gly Gly Gly Ser Gly Gly Gly Gly Ser
1               5                   10                  15
```